(12) United States Patent
Attarian et al.

(10) Patent No.: US 6,962,990 B1
(45) Date of Patent: Nov. 8, 2005

(54) FUSOBACTERIUM NUCLEIC ACIDS, PLASMIDS AND VECTORS

(75) Inventors: Gwynne Attarian, Ann Arbor, MI (US); Kara K. Podkaminer, Jamesville, NY (US); Sean C. Yoder, Chatsworth, CA (US); Susan A. Kinder Haake, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 403 days.

(21) Appl. No.: 09/747,385

(22) Filed: Dec. 22, 2000

Related U.S. Application Data

(60) Provisional application No. 60/173,168, filed on Dec. 27, 1999.

(51) Int. Cl.[7] .................. C07H 21/04; C12N 15/74; C12N 15/70; C07K 14/00
(52) U.S. Cl. ................. 536/24.1; 536/23.1; 435/320.1; 435/476; 435/488; 435/252.3; 435/252.33; 530/350
(58) Field of Search ................ 536/23.1, 24.1; 435/320.1, 476, 488, 252.3, 252.33; 530/350

(56) References Cited

PUBLICATIONS

GenBank Accession No. AF022647, established on Sep. 3, 1997.*
Chang et al. The Journal of Cell Biology 104: 1563–1568, 1987.*
Kelley et al. Endocrine Research 16:477–491, 1990.*
Everett et al. Pendred syndrome is caused by mutations in a putative sulphate transporter gene (PDS). Nature Genetics 17: 411–422, 1997.*
Scott et al. The pendred syndrome gene encodes a chloride–iodide trasnport protein. Nature Genetics 21: 440–443, 1999.*
Kinder Haake et al. Journal of Dental Research 78(abstracts):420; Abstract No. 2498, 1999.*
Kinder Haake et al. Abstracts of the General Meeting of the American Society of Microbiology 99:331, Abstract No. H–9, May 1999.*
McKay et al. Plasmid 33:15–25 1995.*
Sptrembl database result of SEQ ID NO:1 (RepA protein) against RepA sequence disclosed by McKay et al.*

* cited by examiner

*Primary Examiner*—James Ketter
*Assistant Examiner*—David A. Lambertson
(74) *Attorney, Agent, or Firm*—Townsend and Townsend and Crew LLP

(57) ABSTRACT

The invention provides origin of replication sequences and replication genes and proteins for a plasmid functional in *Fusobacterium* (e.g., *F. nucleatum*) and related species. Provided by the invention are also plasmids and vectors that can replicate in *Fusobacterium*. Further, the invention provides shuttle vectors that can replicate in *Fusobacterium* and in other microorganisms, such as *E. coli*. Still further, the present invention provides host cells comprising the plasmids and shuttle vectors, and methods for transformation of the host cells with the plasmid and shuttle vectors of the invention.

63 Claims, 7 Drawing Sheets

FUSOBACTERIUM NUCLEIC ACIDS, PLASMIDS AND VECTORS

CROSS-REFERENCES TO RELATED APPLICATIONS

This application claims priority to provisional application U.S. Ser. No. 60/173,168, filed Dec. 27, 1999, the disclosure of which is herein incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. DE11180 and DE12639, awarded by the National Institutes of Health. The Government has certain rights in this invention.

FIELD OF THE INVENTION

The invention provides origin of replication sequences and replication genes and proteins for a plasmid functional in *Fusobacterium* (e.g., *F. nucleatum*). Provided by the invention are also plasmids and vectors that can replicate in *Fusobacterium* and related species. Further, the invention provides shuttle vectors that can replicate in *Fusobacterium* and in other microorganisms, such as *E. coli*. Still further, the present invention provides host cells comprising the plasmids and shuttle vectors, and methods for transformation of the host cells with the plasmid and shuttle vectors of the invention.

BACKGROUND OF THE INVENTION

*Fusobacterium* species are anaerobic Gram-negative microorganisms that are commonly found in the mouth. *Fusobacterium nucleatum* is the most frequently isolated pathogen from periodontal disease sites and is believed to be an initiator of periodontal diseases (see, e.g., Moore & Moore, *Periodontology* 2000 5:66–77 (1994)). Moreover, this bacterium is commonly found in abscesses and other infections in the abdomen, blood, chest, lung, sinuses, and female genital tract (see, e.g. Brook, *J. Clin. Microbiol.* 26:1181–1188 (1988); Hoist et al., *J. Clin. Microbiol.* 32:176–186 (1994); Moore & Moore, supra). *F. nucleatum* is usually found as a component of polymicrobial infections, but is also found as a single isolate from infections, demonstrating its pathogenic potential. The virulence properties of *F. nucleatum* are related to its adherence to host tissues and other bacterial species, as well as its modulation of host cell immune function (see, Bolstad, *Clin. Microb.* 9:55–71 (1996)) Thus, *F. nucleatum* is a microorganism of interest for further investigation because of its role in the periodontal diseases and other human infectious diseases.

Thus far, several *F. nucleatum* proteins that are believed to be associated with *F. nucleatum* pathogenesis have been cloned and expressed in *Eschericia coli*. For example, a fomA gene that encodes the major outer membrane protein has been cloned. This protein functions as a porin and may act as a receptor in coaggregation with other pathogenic bacteria (see, Jensen et al., *Microb. Path.* 21:331–342 (1996); Kinder Haake et al., *Arch. Oral Biol.* 42:19–24 (1997)). Also cloned is a fipA gene which encodes an immunosuppressive factor that inhibits human T-cell responses (see, Demuth et al., *Infect. Immun.* 64:1335–1341 (1996)). Moreover, a homologous family of small cryptic plasmids in strains of *F. nucleatum* has been isolated (McKay et al., *Plasmid* 33:15–20 (1995)). However, the molecular manipulation of genes in *F. nucleatum* has not been possible due to the lack of reliable gene transfer and expression systems for *F. nucleatum*. The development of gene transfer and expression systems for *F. nucleatum* is essential to express and fully characterize the cloned *F. nucleatum* genes in the native host background.

Therefore, there is a need for reliable gene transfer and expression systems for *F. nucleatum*. The availability of gene transfer and expression systems would assist the molecular characterization of genes that are associated with pathogenesis of *F. nucleatum*. The availability of such systems would further assist the development of compounds that can prevent or treat periodontal diseases or other human infectious diseases caused by *F. nucleatum*. The present invention fulfills this and other needs.

SUMMARY OF THE INVENTION

The present invention provides for the first time origin of replication sequences, repA nucleic acids, and RepA polypeptides of a plasmid functional in *Fusobacterium*, in particular *F. nucleatum*. Also provided by the invention are plasmids and vectors that can replicate in *Fusobacterium*. Further, the invention provides shuttle vectors that can replicate in *Fusobacterium* and in other microorganisms, such as *E. coli*. Still further, the present invention provides host cells comprising these plasmids and shuttle vectors, and methods for transformation of the host cells. Embodiments of the present invention would assist cloning of *F. nucleatum* genes as well as the molecular characterization of genes that are associated with pathogenesis of *F. nucleatum*. Moreover, embodiments of the invention can be used to express foreign genes, such as antigenic determinants of pathogenic microorganism, in *F. nucleatum*. Such transformants can be used as vaccine delivery systems to stimulate mucosal immunity against these pathogens.

In one aspect, the present invention provides isolated origin of replication sequences for *F. nucleatum* that comprise at least two copies of an iteron, wherein the iteron has a nucleic acid sequence of SEQ ID NO:3. In one embodiment, the isolated origin of replication sequences comprise two to six copies of the iteron having a sequence of SEQ ID NO:3. In another embodiment, the isolated origin of replication sequences comprise a nucleic acid sequence of SEQ ID NO:4. In yet another embodiment, the isolated origin of replication sequences comprise a nucleic acid sequence of nucleotide position 3936 to 4481 of plasmid pFN1.

In another aspect, the present invention provides an isolated repA nucleic acid for *F. nucleatum*, wherein the repA nucleic acid encodes a protein that has greater than about 80% amino acid sequence identity to a polypeptide having a sequence of SEQ ID NO:1, or to a polypeptide that selectively binds to polyclonal antibodies generated against SEQ ID NO:1. In one embodiment, the isolated repA nucleic acid encodes a polypeptide having a sequence of SEQ ID NO:1. In another embodiment, the isolated repA nucleic acid encodes a polypeptide that has a molecular weight of about 44.8 kDa. In yet another embodiment, the isolated repA nucleic acid has a sequence of SEQ ID NO:2.

In yet another aspect, the present invention provides an isolated nucleic acid molecule comprising a DNA fragments of plasmid pFN1 or plasmid pFN2. In one embodiment, the isolated nucleic acid molecule comprises a 2.36 kb DNA fragment generated by cleaving plasmid pFN1 with restriction endonucleases AvrII and ScaII. In another embodiment, the isolated nucleic acid molecule comprises a 0.9 kb DNA fragment generated by cleaving plasmid pFN2 with restriction endonucleases HincII and HpaII.

In yet another aspect, the present invention provides an isolated RepA protein that has greater than about 80% amino acid sequence identity to a polypeptide having a sequence of SEQ ID NO:1, or to a polypeptide that selectively binds to polyclonal antibodies generated against SEQ ID NO:1. In one embodiment, the isolated RepA protein has greater than about 97% amino acid sequence identity to a polypeptide having an amino acid sequence of SEQ ID NO:1. In another embodiment, the isolated RepA protein has the amino acid sequence of SEQ ID NO:1.

In yet another aspect, the present invention provides an isolated or recombinant plasmid comprising an origin of replication that comprises at least two copies of an iteron having a nucleic acid sequence of SEQ ID NO:3. In one embodiment, the plasmid comprises an origin of replication that comprises between two to six copies of the iteron having a nucleic acid sequence of SEQ ID NO:3. In another embodiment, the plasmid comprises an origin of replication that comprise a nucleic acid sequence of SEQ ID NO:4.

In yet another aspect, the present invention provides an isolated plasmid comprising a repA nucleic acid, wherein the repA nucleic acid encodes a protein that has greater than about 80% amino acid sequence identity to a polypeptide having a sequence of SEQ ID NO:1, or to a polypeptide that selectively binds to polyclonal antibodies generated against SEQ ID NO:1, provided that the nucleic acid encoding the RepA protein has other than the nucleic acid sequence of SEQ ID NO:5. In one embodiment, the plasmid comprises a repA nucleic acid that encodes a polypeptide having a sequence of SEQ ID NO:1. In another embodiment, the plasmid comprises a repA nucleic acid that has a sequence of SEQ ID NO:2. In yet another embodiment, the plasmid comprises a marker gene, preferably an antibiotic resistance gene.

In yet another aspect, the present invention provides an isolated or recombinant plasmid comprising any combination of origin of replication sequences and repA nucleic acids described herein. For example, in one embodiment, the plasmid comprises an origin of replication sequence comprising SEQ ID NO:4 and a repA nucleic acid that encodes a polypeptide having a sequence of SEQ ID NO:1. In another embodiment, the plasmid further comprises a marker gene, preferably an antibiotic resistance gene.

In yet another aspect, the present invention provides an isolated or recombinant plasmid comprising a DNA fragment derived from plasmid pFN1 or plasmid pFN2. In one embodiment, the plasmid comprises a nucleic acid sequence of nucleotide position 3936 to 4481 of plasmid pFN1. In another embodiment, the plasmid comprises a 2.36 kb DNA fragment which can be generated by cleaving plasmid pFN1 with restriction endonucleases AvrII and ScaII. In yet another embodiment, the plasmid comprises a 0.9 kb DNA fragment which can be generated by cleaving plasmid pFN2 with restriction endonucleases AvrII and ScaII.

In yet another aspect, the present invention provides an isolated plasmid designated pFN1 that has a GenBank Accession No. AF159249. This plasmid has partial restriction maps as shown in FIGS. 1A, 2A, 3 and 5.

In yet another aspect, the present invention provides an isolated plasmid designated pFN2 that have partial restriction maps as shown in FIGS. 1A, 3 and 5.

In yet another aspect, the present invention provides an isolated plasmid designated pFN3 that has a partial restriction map as shown in FIG. 1A.

In yet another aspect, the present invention provides a shuttle vector comprising origin of replication sequences so that the vector can replicate in more than one microorganism. In one embodiment, the shuttle vector comprises an origin of replication functional in *E. coli* and an origin of replication functional in *F. nucleatum*, wherein the origin of replication functional in *F. nucleatum* comprises at least two copies of an iteron having a nucleic acid sequence of SEQ ID NO:3. In another embodiment, the shuttle vector comprises an origin of replication that comprises between two to six copies of the iteron having a sequence of SEQ ID NO:3. In another embodiment, the shuttle vector comprises an origin of replication that comprises a sequence of SEQ ID NO:4. In yet another embodiment, the shuttle vector comprises an origin of replication that comprises a nucleic acid sequence of nucleotide position 3936 to 4481 of plasmid pFN1. In yet another embodiment, the shuttle vector further comprises a repA nucleic acid that encodes a protein that has greater than about 80% amino acid sequence identity to a polypeptide having a sequence of SEQ ID NO:1, or to a polypeptide that selectively binds to polyclonal antibodies generated against SEQ ID NO:1. In yet another embodiment, the shuttle vector comprises a repA nucleic acid that encodes a protein having a sequence of SEQ ID NO:1. In yet another embodiment, the shuttle vector comprises a repA nucleic acid that has a sequence of SEQ ID NO:2. In yet another embodiment, the shuttle vector further comprises a marker gene, preferably an antibiotic resistance gene, more preferably an ermF-ermAM cassette. In yet another embodiment, the shuttle vector further comprises a transcription cassette comprising a nucleic acid of interest operably linked to a promoter. In yet another embodiment, the shuttle vector is plasmid pHS17 that has a nucleotide sequence of SEQ ID NO:15.

In yet another aspect, the invention provides host cells and methods for transformation of host cells with any one or more of plasmids and vectors described herein. In one embodiment, the host cell is *E. coli*. In another embodiment, the host cell is *F. nucleatum*.

DEFINITIONS

Figure 1A:
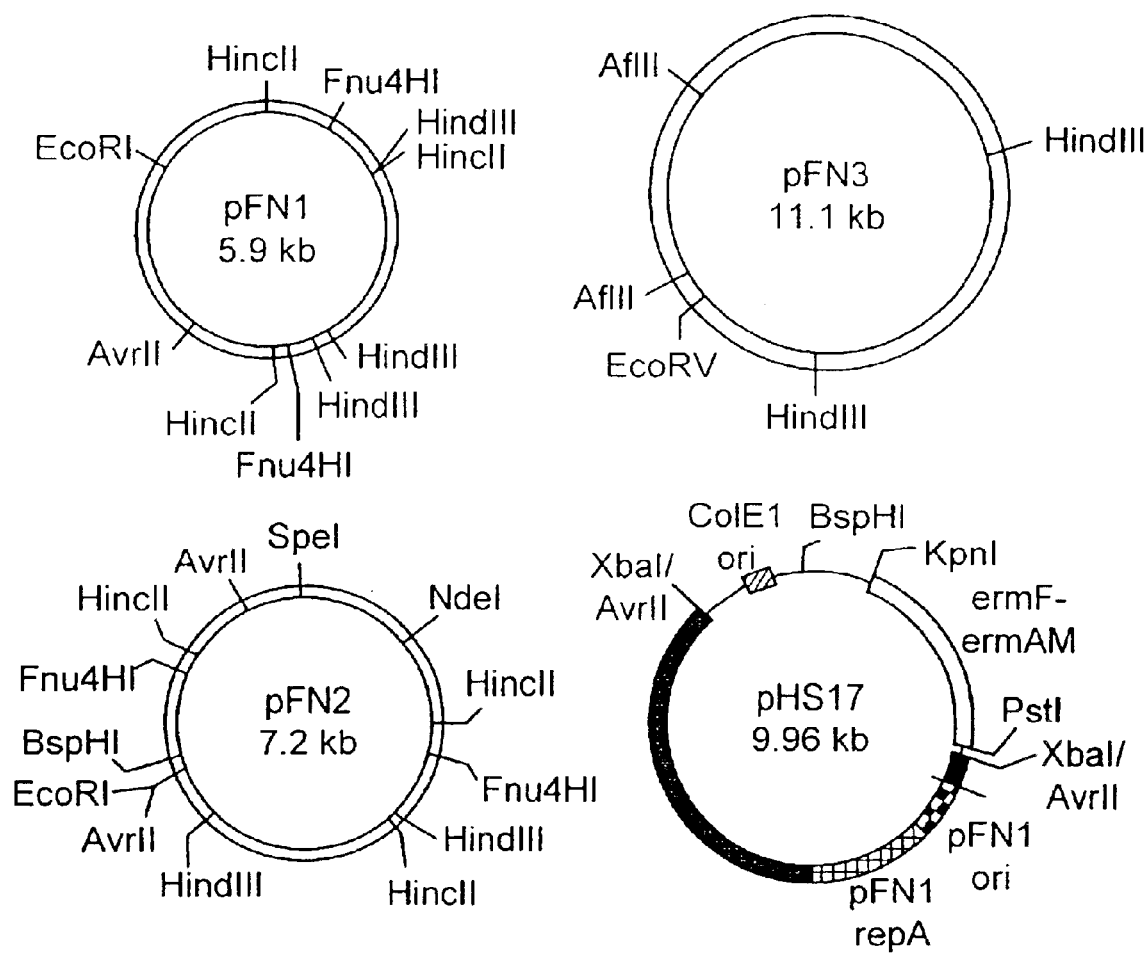
FIG. 1A show partial restriction maps of *F. nucleatum* plasmids pFN1, pFN2, pFN3, and shuttle plasmid pHS17. Selected restriction endonuclease sites in the native plasmids are presented. Restriction endonuclease sites indicated for pHS17 relate to the plasmid construction. The pFN1 portion of pHS17 is indicated by the thick solid bar with the position of the repA homologue (ORF5) and putative ori indicated.

As used herein, the following terms have the meanings ascribed to them unless specified otherwise.

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. For example, an isolated repA nucleic acid is separated from open reading frames that flank the repA gene and encode proteins other than a RepA protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refer to compounds that have the same basic chemical structure as a naturally occurring amino acid, ie., a carbon that is bound to a hydrogen, a carboxyl group, an amino group, and an R group. Exemplary amino acid analogs include, e.g., homoserine, norleucine, methionine sulfoxide, and methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes (A, T, G, C, U, etc.).

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. For example, the following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, *Proteins*, W. H. Freeman and Company (1984)).

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the selected sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous polynucleotide" or a "heterologous nucleic acid," as used herein, is one that originates from a source foreign to the particular host cell, or, if from the same source, is modified from its original form. Thus, a heterologous gene in a host cell includes a gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids of amino acids (e.g., polypeptide) respectively.

A "plasmid" refers to extrachromosomal genetic elements composed of DNA or RNA that are not part of a chromosome but can propagate themselves autonomously in cells. As used herein, a plasmid refers to not only those native plasmids isolated from cells, but also any modified versions (e.g., has deletions, additions or substitutions) so long as they retain the ability to propagate themselves autonomously in cells. Moreover, the term "isolated plasmid" refers to a plasmid that is substantially or essentially free from components which normally accompany it as found in its native state. The term "isolated plasmid" also includes, among other things, modified versions of natural plasmids (e.g., has deletions, additions or substitutions of nucleic acids) or recombinant plasmids.

A "vector" refers to a carrier DNA molecule into which a nucleic acid sequence can be inserted for introduction into a new host cell where it will be replicated, and in some cases expressed. Vectors can be derived from plasmids, bacteriophages, plant, animal viruses, etc.

An "expression vector" is a nucleic acid construct, generated recombinantly or synthetically, with a series of specified nucleic acid elements that permit transcription of a particular nucleic acid in a host cell. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, 95%, 97%, 98%, or 99%) identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, preferably over a region that is at least about 75 amino acids or nucleotides in length, and most preferably over a region that is at least about 100 amino acids or nucleotides in length. In most preferred embodiments, the sequences are substantially identical over the entire length of, e.g., the coding region.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see, Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

A further indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

An "anti-RepA antibody" is an antibody or antibody fragment that specifically binds a polypeptide encoded by a repA gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a RepA protein with the amino acid sequence of a region encoded in SEQ ID NO:1 can be selected to obtain only those polyclonal antibodies that are specifically immunoreactive with the region of the RepA protein and not with other proteins, except for, e.g., homologs or variants of the RepA protein. This selection may be achieved by subtracting out antibodies that cross react with molecules such as other RepA proteins. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "host cell" is meant that a cell that contains a plasmid or a vector and supports the replication or expression of the plasmid or the vector. Host cells include, but are not limited to, *E. coli, F. nucleatum, Leptotrichia, Streptococcus, Staphylococcus, Clostridium*, etc.

THE DETAILED DESCRIPTION OF THE INVENTION

The invention provides novel plasmid origin of replication sequences and replication genes and proteins (hereinafter referred to as "repA" for nucleic acids and "RepA" for polypeptides) that are functional in *Fusobacterium* (e.g., *F. nucleatum*). Also provided by the invention are plasmids and vectors that can replicate in *Fusobacterium* and related species. In some embodiment, the plasmids and vectors of the invention comprise additional origin of replication sequences so that they can replicate in other microorganisms, such as *E. coli*. Further, the invention provides host cells and methods of transforming the host cells using the plasmids and vectors of the present invention.

The above-described embodiments of the invention are useful for several purposes. The origin of replication sequences and repA nucleic acids can be used to construct cloning and expression plasmids and vectors that are functional in *Fusobacterium* as well as in other microorganisms, such as *E. coli*. The plasmids and vectors of the invention can be used, e.g., for cloning of *F. nucleatum* nucleic acids as well as expression of these genes in the native host background. The plasmids and vectors can also be used for cloning and/or expression of foreign genes. Moreover, the plasmids and vectors of the invention can be used in the development of vaccine delivery systems. For example, foreign genes that encode, e.g., an antigenic determinant of a pathogenic organism can be introduced into the plasmids or vectors of the invention. *F. nucleatum* transformed with these plasmids or vectors can be introduced into the oral cavity as a vaccine delivery system to stimulate mucosal immunity against these pathogens.

I. Isolation of Plasmid Origin of Replication Sequences and repA Nucleic Acids

A. Origin of Replication Sequences for *Fusobacterium* Plasmids

In one aspect, the invention provides origin of replication sequences of a plasmid functional in *Fusobacterium*. An origin of replication in a plasmid provides a region at which specific proteins bind to the open DNA complex, thereby initiating the plasmid DNA replication process. The origin of replication sequences of the invention are useful for several purposes. For example, the origin of replication sequences of the invention are useful as probes to identify other plasmid origin of replication sequences. In another example, the origin of replication sequences can be used to construct a plasmid or a vector that can replicate in *Fusobacterium* (e.g., *F. nucleatum*). The origin of replication sequences can also be used to construct a shuttle vector that can replicate in *Fusobacterium* as well as in other microorganisms, such as *E. coli*.

An example of an origin of replication sequences of the invention is isolated from *Fusobacterium* species, such as *F. nucleatum*. A presently preferred origin of replication sequence comprises a nucleic acid as shown in SEQ ID NO:4 and is derived from plasmid pFN1 of *F. nucleatum* strain 12230 (a gift from S. Finegold, West Los Angeles, Va.). As shown in the Sequence Listing, SEQ ID NO:4 contains six perfect 22 base pair direct repeats ("iterons"). The 22 base pair iteron is given SEQ ID NO:3.

The origin of replication sequences of the present invention generally include those that comprise at least two copies of the iteron, wherein the iteron has the nucleic acid sequence of SEQ ID NO:3. Preferably, the origin of replication sequences of the invention comprise between two to six copies of the iteron having the nucleic acid sequence of SEQ ID NO:3. More preferably, the origin of replication sequences of the invention comprise a nucleic acid sequence of SEQ ID NO:4 (i.e., six copies of the iteron having SEQ ID NO:3, which six copies span the nucleotide positions 4169 to 4300 of plasmid pFN1). In some embodiments, the origin of replication sequences can comprise imperfect repeats of the iteron having SEQ ID NO:3. For example, the origin of replication sequences can comprise nucleic acids as shown in SEQ ID NOs: 11, 12, 13, or any combinations thereof. Moreover, the origin of replication can further comprise other sequences, such as DnaA binding site sequences and A-T rich regions as shown in FIG. 3B. For instance, in some embodiments the origin of replication sequences can comprise the nucleotide position 3936 to 4481 of plasmid pFN1. This fragment of plasmid pFN1 comprises six copies of the iterons as well as the DnaA binding site sequences and A-T rich regions.

To identify origin of replication sequences of the invention, one can use visual inspection or can use a suitable algorithm as described herein. Alternatively, one can identify origin of replication sequences of the invention by hybridizing, under stringent conditions, the candidate nucleic acids to the origin of replication sequences (e.g., a sequence comprising SEQ ID NO:4).

B. repA Nucleic Acids for *Fusobacterium* Plasmids

In another aspect, the invention provides repA nucleic acids encoding RepA polypeptides that can bind to origin of replication sequences in a plasmid of *Fusobacterium*. Not wishing to be bound by a theory, the RepA polypeptides encoded by the repA nucleic acids bind to the iteron sequences in the origin of replication of a plasmid. The binding results in structural changes, including melting of the adjacent A-T rich region, to form an open complex. The RepA polypeptides, possibly in conjunction with the host DnaA protein, then guide host replication proteins into the open complex, and thereby initiating the plasmid DNA replication process.

The repA nucleic acids of the invention are useful for several purposes. For example, repA nucleic acids can be used to recombinantly express RepA polypeptides. These RepA polypeptides can then be used as immunogens to produce anti-RepA polypeptide antibodies. The repA nucleic acids can also be used as probes to identify other repA nucleic acids. Moreover, the repA nucleic acids of the invention can be used to construct a plasmid or a vector functional in *Fusobacterium*.

An example of a repA nucleic acid of the invention is produced by *Fusobacterium* species, such as *F. nucleatum*. A presently preferred repA nucleic acid is that of plasmid pFN1, which has a nucleic acid sequence as shown in SEQ ID NO:2 and encodes a polypeptide of 407 amino acids as shown in SEQ ID NO:1. Plasmid pFN can be isolated from *F. nucleatum* strain 12230 (a gift from S. Finegold, West Los Angeles, Va.). The repA nucleic acid is located at nucleotide position 4508 to 5731 of plasmid pFN1, and contains putative promoters at −35 and −10 nucleotide positions.

The repA nucleic acids of the invention generally include those that encode a RepA polypeptide having an amino acid sequence that is at least about 80% identical to an amino acid sequence as set forth in SEQ ID NO:1 over a region of at least about 50 amino acids in length. Preferably, the RepA polypeptides encoded by the nucleic acids of the invention are at least about 85% identical to an amino acid sequence of SEQ ID NO:1, more preferably are at least about 90% identical to an amino acid sequence of SEQ ID NO:1, still more preferably are at least about 95% identical to an amino acid sequence of SEQ ID NO:1, and most preferably are at least about 96%, 97%, 98%, or 99% identical to an amino acid sequence of SEQ ID NO:1, over a region of at least 50 amino acids in length. In preferred embodiments, the region of percent identity extends over a region longer than 50 amino acids, preferably over a region of at least about 75 amino acids, more preferably over a region of at least about 100 amino acids, and most preferably over the full length of the RepA polypeptide. In a preferred embodiment, the repA nucleic acids of the invention encode a polypeptide having an amino acid sequence as shown in SEQ ID NO:1.

Moreover, the repA nucleic acids of the invention are typically at least about 80% identical to a nucleic acid sequence of SEQ ID NO:2 over a region of at least about 50 nucleotides in length. Preferably, the repA nucleic acids of the invention are at least about 85% identical to a nucleic acid of SEQ ID NO:2, more preferably are at least about 90% identical to a nucleic acid of SEQ ID NO:2, and most preferably are at least about 95% identical to a nucleic acid of SEQ ID NO:2, over a region of at least about 50 nucleotides in length. In preferred embodiments, the region of percent identity extends over a region longer than 50 nucleotides, preferably over a region of at least about 75 nucleotides, more preferably over a region of at least about 100 nucleotides, and most preferably over the full length of the RepA encoding region.

To identify repA nucleic acids of the invention, one can use visual inspection or can use a suitable alignment algorithm as described herein, such as the BLASTN Version 2.0 algorithm. An alternative method by which one can identify a repA nucleic acid of the invention is by hybridizing, under stringent conditions, the candidate repA nucleic acids to the repA nucleic acids described herein (e.g. a sequence comprising a sequence of SEQ ID NO:2).

C. Methods for Isolation of Nucleic Acids

The origin of replication sequences or repA nucleic acids of the invention can be obtained using methods that are known to those of skill in the art. Suitable nucleic acids (e.g., cDNA, plasmid, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger & Kimmel, *Guide to Molecular Cloning Techniques, Methods in Enzymology* 152 Academic Press, Inc., San Diego, Calif. (Berger); Sambrook et al., *Molecular Cloning—A Laboratory Manual* (2nd ed.) Vol. 1–3, Cold Spring Harbor Laboratory, Cold Spring Harbor Press, NY (1989); *Current Protocols in Molecular Biology*, Ausubel et al., eds., Current Protocols, a joint venture between Greene Publishing Associates, Inc. and John Wiley & Sons, Inc., (1994 Supplement); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; PCR *Protocols A Guide to Methods and Applications* (Innis et al., eds) Academic Press Inc. San Diego, Calif. (1990) (Innis); Arnheim & Levinson C&EN 36–47 (Oct. 1, 1990); *The Journal Of NIH Research* 3: 81–94 (1991); Kwoh et al. *Proc. Natl. Acad. Sci. USA* 86: 1173 (1989); Guatelli et al., *Proc. Natl. Acad. Sci. USA* 87 (1990), 1874; Lomell et al., *J. Clin. Chem.*, 35: 1826 (1989); Landegren et al., *Science* 241: 1077–1080 (1988); Van Brunt, *Biotechnology* 8: 291–294 (1990); Wu & Wallace, *Gene* 4: 560 (1989); and Barringer et al., *Gene* 89: 117 (1990). Improved methods of cloning in vitro amplified nucleic acids are described in Wallace et al, U.S. Pat. No. 5,426,039.

Origin of replication sequences or repA nucleic acids of the invention, or subsequences thereof can be obtained using any suitable method as described above, including, for example, cloning and restriction of appropriate sequences. In cloning methods, a known nucleotide sequence of an origin of replication, such as those described herein, can be used to provide probes that specifically hybridize to other nucleic acids that encode an origin of replication in a plasmid DNA samples. Similarly, a known nucleotide sequence of a repA gene, such as those described herein, can be used to provide probes that specifically hybridize to a gene that encodes a RepA polypeptide in a plasmid DNA sample, or to a mRNA in a total RNA sample (e.g., in a Southern or Northern blot). Preferably, the samples are obtained from prokaryotic organisms, such as *Fusobacterium* species. Examples of *Fusobacterium* species of particular interest include *F. nucleatum, F. necrophorum, F. varium, F. periodonticum*, etc.

Once the target nucleic acid is identified, it can be isolated according to standard methods known to those of skill in the art (see, e.g., Sambrook et al., *Molecular Cloning: A Laboratory Manual, 2nd Ed., Vols.* 1–3, Cold Spring Harbor Laboratory (1989); Berger and Kimmel, *Methods in Enzymology, Vol.* 152: *Guide to Molecular Cloning Techniques*, San Diego: Academic Press, Inc. (1987); or Ausubel et al., *Current Protocols in Molecular Biology*, Greene Publishing and Wiley-Interscience, New York (1987).

The origin of replication sequences, repA nucleic acids, or subsequences thereof can also be cloned using DNA amplification methods such as polymerase chain reaction (PCR). For example, the nucleic acid sequence or subsequence of an origin of replication or a repA gene is PCR amplified, preferably using a sense primer containing one restriction site (e.g., XbaI) and an antisense primer containing another restriction site (e.g., HindIII). This will produce an origin of replication nucleic acid, a repA nucleic acid, or a subsequence thereof, having terminal restriction sites. This nucleic acid can then be ligated into a vector containing a nucleic acid encoding the second molecule and having the appropriate corresponding restriction sites. Suitable PCR primers can be determined by one of skill in the art using the sequence information provided herein. Examples of suitable primers for amplification of the origin of replication sequences or repA nucleic acids are provided in Example 4. Appropriate restriction sites can also be added to the origin of replication sequences or repA nucleic acids, by site-directed mutagenesis. The plasmid containing the origin of replication sequences, repA nucleic acids, and/or subsequences thereof is cleaved with the appropriate restriction endonuclease and then ligated into an appropriate vector for amplification and/or expression according to standard methods.

Since repA nucleic acids encode detectable polypeptides, these nucleic acids can also be cloned by detecting their expressed RepA polypeptides using assays based on, e.g., immunological properties. For example, one can identify a cloned repA nucleic acid by screening expression libraries using antibodies as probes. Such polyclonal or monoclonal antibodies can be raised using a sequence or a subsequence of, e.g., SEQ ID NO:1.

As an alternative to cloning the origin of replication sequences or repA nucleic acids, a suitable nucleic acid can be chemically synthesized from known sequences of origin of replication or repA of the invention (e.g., SEQ ID NO:4 or SEQ ID NO:2, respectively). Direct chemical synthesis methods include, for example, the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments can then be ligated to produce the desired DNA sequence.

In some embodiments, it may be desirable to modify the origin of replication sequences or repA nucleic acids. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids)

and other well-known techniques. See, e.g., Giliman & Smith, *Gene* 8:81–97 (1979); Roberts et al., *Nature* 328: 731–734 (1987).

III. Isolation of RepA Polypeptides

In yet another aspect, the invention provides RepA polypeptides that bind to an origin of replication sequence of a plasmid in *Fusobacterium*. An example of a RepA polypeptide of the invention is produced by *Fusobacterium* species, such as *F. nucleatum*. A presently preferred RepA polypeptide has an amino acid sequence as shown in SEQ ID NO:1 (consisting of 407 amino acids) and has an approximate molecular weight of 44.8 kDa The RepA polypeptides of the invention can be purified from natural sources, e.g., *F. nucleatum* strain 12230 (a gift from S. Finegold, West Los Angeles), or can be recombinantly made. Methods for recombinant production or purification of RepA polypeptides are well known in the art. Substantially pure compositions of at least about 90 to 95% homogeneity are preferred for some applications, and 98 to 99% or more homogeneity are most preferred. Once purified, partially or to homogeneity as desired, the RepA polypeptides may then be used, e.g., as immunogens for antibody production.

The RepA polypeptides of the invention generally include an amino acid sequence that is at least about 80% identical to an amino acid sequence as set forth in SEQ ID NO:1 over a region at least about 50 amino acids in length. Preferably, the RepA polypeptides of the invention are at least about 85% identical to the amino acid sequence of SEQ ID NO:1, more preferably are at least about 90% identical to the amino acid sequence of SEQ ID NO:1, still more preferably are at least about 95% identical to the amino acid of SEQ ID NO:1, and most preferably are at least about 96%, 97%, 98%, 99% identical to the amino acid of SEQ ID NO:1, over a region of 50 amino acids in length. In presently preferred embodiments, the region of percent identity extends over a region of at least about 50 amino acids, preferably over a region of at least about 75 amino acids, more preferably over a region of at least about 100 amino acids, and most preferably over the full length of the RepA polypeptide.

To identify RepA polypeptides of the invention, one can use visual inspection or can use a suitable alignment algorithm as described above, such as the BLASTP Version 2.0 algorithm. Alternatively, the RepA polypeptides of the invention can also be identified by immunoreactivity. For example, one can produce RepA antibodies against an antigenic determinant of the RepA polypeptide having SEQ ID NO:1 and determine whether the antibodies are specifically immunoreactive with a RepA polypeptide of interest.

The RepA polypeptides of the invention can be isolated from natural sources (e.g., from *F. nucleatum*) or synthesized using the recombinant nucleic acid or chemical synthesis methodologies. These methodologies are well known in the art. If recombinant expression is desired, the repA nucleic acid sequences of the invention described above can be operably linked to appropriate control sequences for expression in a host cell (e.g., bacterial, yeast, plant, fungi, or mammalian cells). For example, if *E. coli* or *F. nucleatum* is used as a host cell, the repA nucleic acid sequences are operably linked to a promoter, a ribosome binding site and preferably, a transcription termination signal. The repA nucleic acid sequence operably linked to control sequences is introduced into an appropriate plasmid or a vector for expression of RepA polypeptides in a host cell.

Once expressed, the naturally occurring or recombinant RepA polypeptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology Vol. 182: Guide to Polypeptide Purification* (1990)).

If chemical synthesis is desired, the RepA polypeptides can be synthetically prepared via a wide variety of well-known techniques. Polypeptides of relatively short size are typically synthesized in solution or on a solid support in accordance with conventional techniques (see, e.g., Merrifield, *Am. Chem. Soc.* 85:2149–2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3–284 in *The Peptides: Analysis, Synthesis, Biology. Vol. 2: Special Methods in Peptide Synthesis, Part A.*; Merrifield et al., *J. Am. Chem. Soc.* 85:2149–2156 (1963); and Stewart et al., *Solid Phase Peptide Synthesis* (2nd ed. 1984).

After chemical synthesis, biological expression or purification, the RepA polypeptide may possess a conformation substantially different than the native conformations of the constituent polypeptides. In this case, it is helpful to denature and reduce the RepA polypeptide and then to cause the polypeptide to re-fold into the preferred conformation. Methods of reducing and denaturing polypeptides and inducing refolding are well known to those of skill in the art (see, Debinski et al., *J. Biol. Chem.* 268:14065–14070 (1993); Kreitman & Pastan, *Bioconjug. Chem.* 4:581–585 (1993); and Buchner et al., *Anal. Biochem.* 205:263–270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the RepA polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids placed on either terminus to create conveniently located restriction sites or termination codons or purification sequences.

III. Immunological Detection of RepA Polypeptides

In addition to the detection of repA genes using the nucleic acid hybridization technology, one can also use immunoassays to detect RepA polypeptides. Immunoassays can be used to qualitatively or quantitatively analyze RepA polypeptides. A general overview of the applicable technology can be found in Harlow & Lane, *Antibodies: A Laboratory Manual* (1988). See, also, U.S. Pat. Nos. 4,366,241; 4,376,110; 4,517,288; and 4,837,168. Useful assays include, for example, an enzyme immune assay (EIA) such as enzyme-linked immunosorbent assay (ELISA), a radioimmune assay (RIA), a Western blot assay, or a slot blot assay. For a review of the general immunoassays, see also, *Methods in Cell Biology: Antibodies in Cell Biology*, volume 37 (Asai, ed. 1993); *Basic and Clinical Immunology* (Stites & Terr, eds., 7th ed. 1991).

Antibodies that specifically bind to a RepA polypeptide can be prepared using any suitable methods known in the art.

See, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Specific polyclonal antisera and monoclonal antibodies will usually bind with a Kd of at least about 0.1 mM, more usually at least about 1 $\mu$M, preferably at least about 0.1 $\mu$M or better, and most preferably, 0.01 $\mu$M or better.

After the antibody is provided, a sample comprising the RepA polypeptides can be contacted with the antibody. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. After contacting the sample with the antibody, the mixture is incubated for 10 seconds to 12 hours, preferably from about 30 seconds to about 30 minutes.

After incubation, the mixture is washed and the presence or amount of antibody-RepA polypeptide complex formed is determined. This can be accomplished by incubating the washed mixture with a detection reagent (e.g., a second, labeled antibody). This detection reagent may be a monoclonal or polyclonal antibody and is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the presence or amount of RepA polypeptides in the sample can be determined using an indirect assay, wherein, for example, a second, labeled antibody is used to detect bound antibody, and/or in a competition or inhibition assay wherein, for example, a monoclonal antibody which binds to a distinct epitope of the marker are incubated simultaneously with the mixture. These techniques are well-known in the art and are within the skill of those in the art.

To determine if a protein specifically binds to the polyclonal antibodies generated to RepA polypeptides or fragments thereof, immunoassays in the competitive binding format can be used. For example, a protein having an amino acid sequence of SEQ ID NO:1 or a fragment thereof can be immobilized to a solid support. Other proteins (candidate RepA polypeptides) are added to the assay so as to compete for binding of antisera to the immobilized antigen. The ability of the added proteins to compete for binding of the antisera to the immobilized protein is compared to the ability of the RepA polypeptide having SEQ ID NO:1 or a fragment thereof compete with itself. The percent crossreactivity of the above proteins is calculated, using standard calculations. Those antisera with less than 10% crossreactivity with each of the added proteins listed above are selected and pooled. The cross-reacting antibodies are optionally removed from the pooled antisera by immunoabsorption with the added proteins, e.g., distantly related homologs.

The immunoabsorbed and pooled antisera are then used in a competitive binding immunoassay to compare a second protein, thought to be a homolog of RepA polypeptide, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein having an amino acid sequence of SEQ ID NO:1 or a fragment thereof that is required to inhibit 50% of binding, then the second protein is said to specifically bind to the polyclonal antibodies generated to the RepA polypeptide of the invention.

IV. Isolation of *Fusobacterium* Plasmids

In yet another aspect, the invention provides plasmids that can be stably maintained in *Fusobacterium*. The plasmids of the invention include, for example, those that are isolated from the natural source (e.g., *F. nucleatum*), modified plasmids (e.g., have substitution, deletion or addition of sequences) or recombinant plasmids. These plasmids are useful for several purposes. For example, they can be used as a cloning or expression system for *Fusobacterium*. The plasmids of the invention can also be used to construct a shuttle vector that can replicate in *Fusobacterium*, as well as in another microorganism, such as *E. coli*.

The plasmids of the invention can be purified from natural sources, e.g., *Fusobacterium* species described herein. In preferred embodiments, plasmids are obtained from *F. nucleatum*. Methods by which the plasmids can be isolated include standard plasmid DNA miniprep methods including, e.g., the alkaline lysis prep, the boiling methods and a lithium-based procedure (see, e.g., Ausubel et al., supra.). Alternatively, the plasmids of the invention can be recombinantly produced. For example, plasmid pFN1 or its derivative can be produced recombinantly using the sequence information disclosed herein. A number of cloning and in vitro amplification methodologies described above can also be used to produce plasmids of the invention.

Embodiments of the present plasmids can be isolated from *Fusobacterium* species, such as *F. nucleatum*. These plasmids include, e.g., pFN1, pFN2 and pFN3. Plasmid pFN1 can be isolated from, e.g., *F. nucleatum* strain 12230 (a gift from S. Finegold, West Los Angeles, Va.). Plasmid pFN1 is characterized by a length of about 5.9 kb (see, GenBank Accession No. AF159249) and has partial restriction maps as shown in FIGS. 1A, 2, 3 and 5. For the partial restriction map shown in FIG. 1A, the number of cleavage sites for each restriction enzyme and the length of fragments generated by the restriction enzymes for pFN1 are as follows:

TABLE 1

| Restriction Enzymes | Number of Cleavage Sites | DNA Fragments (kb) |
|---|---|---|
| HincII | 3 | 1.9, 2.9, 1.1 |
| Fnu4HI | 2 | 2.3, 3.6 |
| HindIII | 3 | 1.5, 0.1, 4.3 |
| AvrII | 1 | 5.9 |
| EcoRI | 1 | 5.9 |

Figure 3:
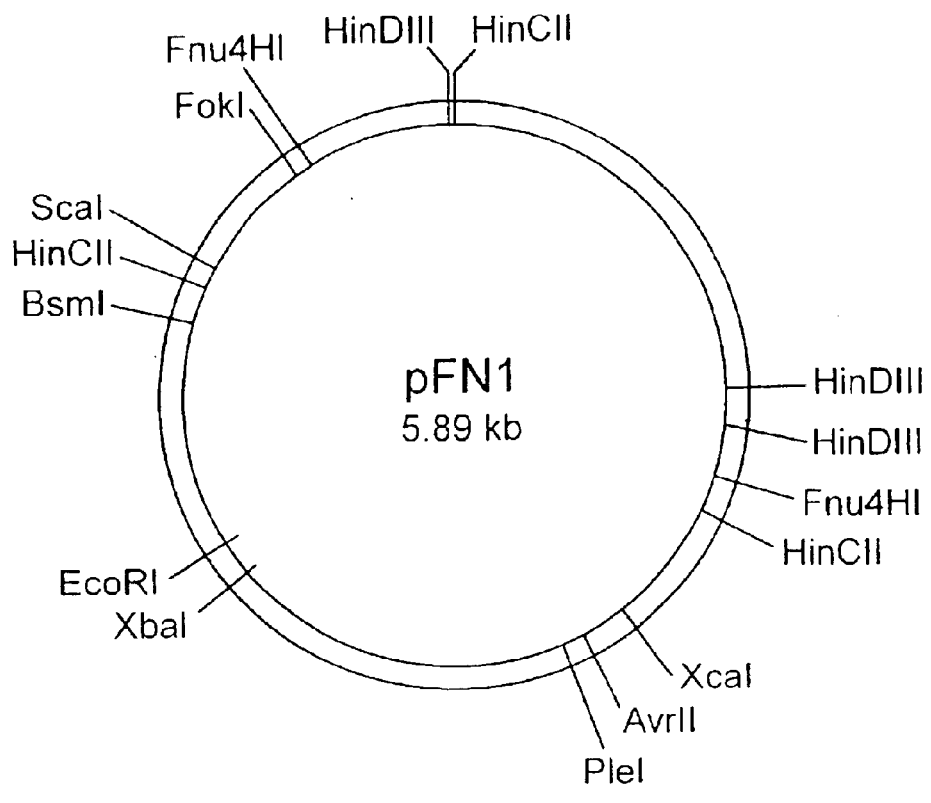
FIG. 3 shows another partial restriction maps of plasmids pFN1 and pFN2. Restriction endonuclease sites of selected enzymes are indicated.
Figure 3:
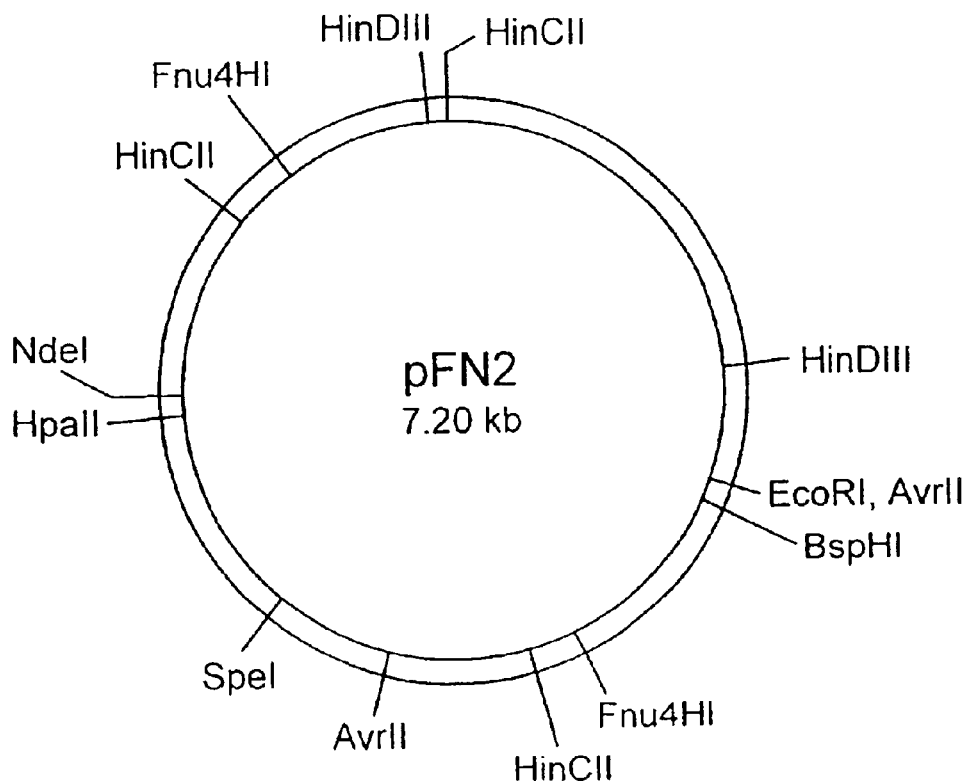
Figure 5:
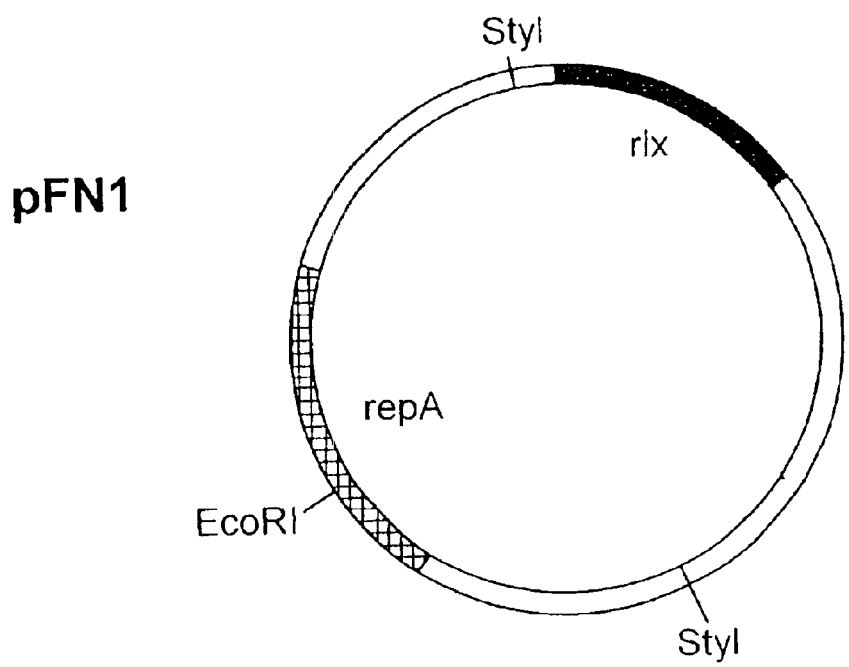
FIG. 5 shows localization of repA and rlx homology on pFN2. Restriction maps of pFN1 and pFN2 indicate the positions of selected restriction endonuclease sites, the repA and rlx genes of pFN1, and the repA and rlx homologous regions of pFN2.
Figure 5:
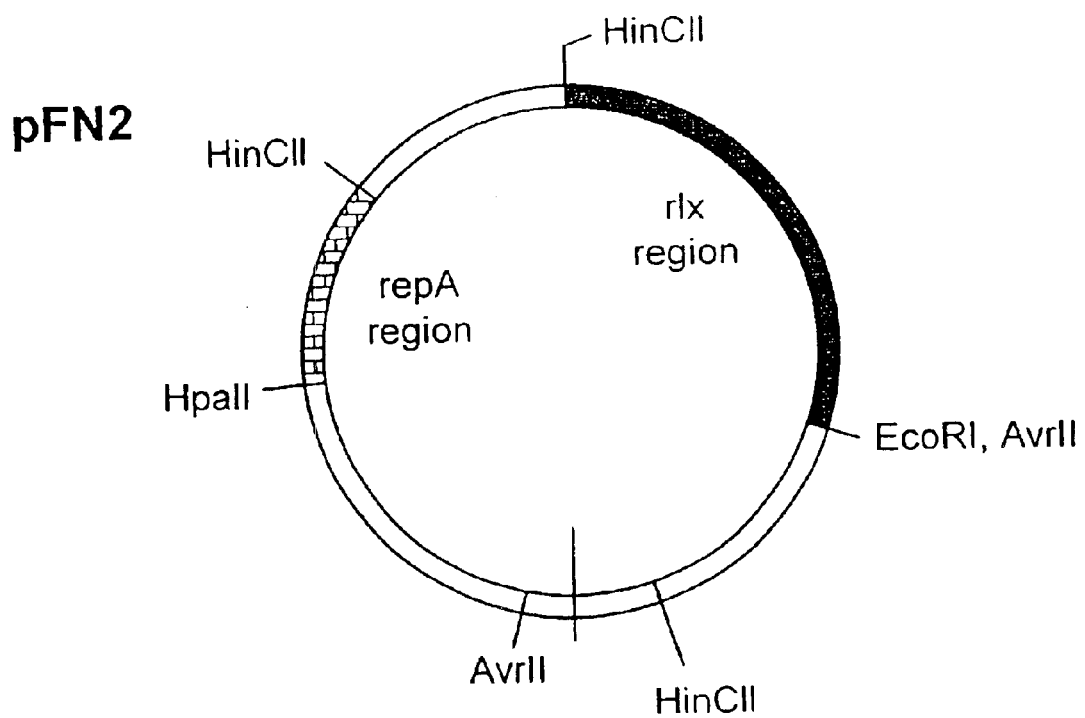

Plasmid pFN2 can be isolated from, e.g., *F. nucleatum* ATCC strain deposit number PTA-5816, deposited under the Budapest Treaty with the American Type Culture Collection (ATCC), 10801 University Blvd. Manassas. VA 20110–2209. Plasmid pFN2 is characterized by a length of about 7.2 kb and has partial restriction maps as shown in FIGS. 1A, 3 and 5. For the partial restriction map shown in FIG. 1A, the number of cleavage sites for each restriction enzyme and the length of fragments generated by the restriction enzymes for pFN2 are as follows:

TABLE 2

| Restriction Enzymes | Number of Cleavages | DNA Fragments (kb) |
| --- | --- | --- |
| SpeI | 1 | 7.2 |
| NdeI | 1 | 7.2 |
| HincII | 3 | 1.0, 2.8, 3.4 |
| Fnu4HI | 2 | 3.8, 3.4 |
| HindIII | 2 | 5.4, 1.8 |
| AvrII | 2 | 5.5, 1.7 |
| EcoRI | 1 | 7.2 |
| BspHI | 1 | 7.2 |

Plasmid pFN3 can be isolated from, e.g., *F. nucleatum* ATCC strain deposit number PTA-5815, deposited under the Budapest Treaty with the American Type Culture Collection (ATCC), 10801 University Blvd. Manassas. VA 20110-2209. Plasmid pFN3 is characterized by a length of about 11.1 kb and has a partial restriction map as shown in FIG. 1A. The nucleotide sequence of plasmid pFN3 has been partially determined and is shown as SEQ ID NO: 14. The number of cleavage sites for each restriction enzyme and the length of fragments generated by the restriction enzymes for pFN3 are as follows:

TABLE 3

| Restriction Enzyme | Number of Cleavage Sites | DNA Fragments (kb) |
| --- | --- | --- |
| HindIII | 2 | 3.4, 7.7 |
| EcoRV | 1 | 11.1 |
| AflII | 2 | 2.1, 9.0 |

Each of these plasmids comprises an origin of replication and a repA nucleic acid which allows them to replicate in *Fusobacterium*. For example, plasmid pFN1 comprises an origin of replication and repA nucleic acid sequences within the 2.36 kb restriction segment between restriction sites AvrII and ScaI (see, FIG. 2A). In another example, a 0.9 kb restriction segment between restriction sites HincII and HpaII of plasmid pFN2 shown in FIG. 3 hybridizes to the repA probe of plasmid pFN1, indicating that repA nucleic acid of plasmid pFN2 is located within this 0.9 kb restriction segment.

Any other plasmids derived from, e.g., any one of pFN1, pFN2 and pFN3 are within the embodiments of the invention, as long as they contain necessary regions for replication in *Fusobacterium*. For example, these derivatives can be derived either by the deletion of unnecessary regions of replication from these plasmids, or by insertion or addition of any other DNA to these plasmids, or substitution of sequences in the regions for replication. Therefore, embodiments of the invention are not limited to plasmids pFN1, pFN2 and pFN3 themselves, but include other derivative plasmids by modifying these plasmids as well as other recombinant plasmids obtained by insertion of other nucleic acids, e.g., marker genes, promoters, other origin of replication sequences, etc. The recombinant methods for production of these plasmids and vectors are described in detail below.

V. Construction of Recombinant Plasmids and Vectors

In yet another aspect, the invention provides recombinant plasmids and vectors that are functional in *Fusobacterium*. The invention also provides plasmids and vectors that are functional in *Fusobacterium* as well as in other microorganisms, such as *E. coli*. The plasmids and vectors of the invention can be used for cloning and expressing *Fusobacterium* genes. The plasmids and vectors of the invention can also be used express foreign genes in *Fusobacterium* or in other microorganisms.

The recombinant plasmids and vectors can be produced by joining the nucleic acids, plasmids or fragments described herein and other nucleotide sequences using recombinant methods known in the art. Typically, a plasmid or a vector of the invention comprises an origin of replication functional in *Fusobacterium* (e.g., *F. nucleatum*), convenient restriction endonuclease sites and one or more selectable markers. Other elements can be included depending on the desired use of a vector.

A plasmid or a vector of the invention can comprise any origin of replication sequences described herein. For example, a plasmid or a vector comprises an origin of replication comprising at least two copies of the iteron, wherein the iteron has a nucleic acid sequence of SEQ ID NO:3. Preferably, a plasmid or a vector comprises an origin of replication comprising at least two to six copies of the iteron having a nucleic acid sequence of SEQ ID NO:3. More preferably, a plasmid or vector of the invention comprises a nucleic acid sequence of SEQ ID NO:4. Alternatively, restriction fragments of plasmids pFN1, pFN2 or pFN3 that contain the origin of replication sequences can be ligated to provide a recombinant plasmid or vector of the invention.

A plasmid or a vector of the invention can also comprise any suitable repA nucleic acids for *F. nucleatum* described herein that are compatible with the origin of replication sequences of the plasmid or vector, provided that the repA nucleic acids have other than the nucleic acid sequence of SEQ ID NO:5 (a nucleic acid of plasmid pAD52 that encodes a RepA homolog; see, GenBank Accession No. AF022647, the nucleotide positions 1108 through 2337). For example, a plasmid or a vector of the invention comprises a repA nucleic acid that encodes an amino acid sequence that is at least about 80%, preferably at least about 85%, more preferably at least about 90%, most preferably at least about 95%, 96%, 97%, 98% or 99%, identical to an amino acid as set forth in SEQ ID NO:1 over a region of at least about 50 amino acids in length. Alternatively, a plasmid or a vector of the invention comprises a repA nucleic acid that is at least about 80%, preferably at least about 85%, more preferably at least about 90%, most preferably at least about 95%, 96%, 97%, 98% or 99% identical to a nucleic acid as set forth in SEQ ID NO:2. In preferred embodiments, the region of identity extends over a region longer than 50 amino acids or nucleotides, preferably over a region of at least about 75 amino acids or nucleotides, more preferably over a region of at least about 100 amino acids or nucleotides, most preferably over the full length of the repA amino acid or nucleotide sequence. In preferred embodiments, a plasmid or a vector of the invention comprises a repA nucleic acid that encodes a polypeptide having the amino acid sequence of SEQ ID NO:1 or has a nucleic acid sequence of SEQ ID NO:2. These repA nucleic acids are operably linked to a promoter and other regulatory sequences in a plasmid or a vector in any suitable manner.

In yet another embodiment, a vector can comprise any combination of origin of replication sequences and repA nucleic acid sequences described above. For example, a vector can comprise an origin of replication comprising a nucleic acid sequence of SEQ ID NO:4 and a repA nucleic acid sequence comprising a nucleic acid sequence of SEQ ID NO:2. In another example, a vector can comprise a 2.36 kb fragment between restriction sites AvrII and ScaII derived from plasmid pFN1 (or conservatively modified variants thereof) and a repA nucleic acid comprising a nucleic acid sequence of SEQ ID NO:2. In yet another example, a vector can comprise a nucleic acid comprising an origin of replication at nucleotide position 3936 to 4481 of plasmid pFN1 and a 0.9 kb fragment between restriction sites HincII and HpaII derived from plasmid pFN2 (or conservatively modified variants thereof) that comprises repA nucleic acid sequences.

In some embodiments, a plasmid or a vector can be a shuttle vector comprising additional origin of replication sequences so that it can replicate in *Fusobacterium* as well as in another microorganism. Such sequences are well known for a variety of microorganisms, including, e.g., Gram-negative or Gram-positive bacteria. For instance, the origin of replication sequences in pBR or pUC series plasmids can be ligated to produce a shuttle vector of the invention. Preferably, additional origin of replication sequences are selected so that a shuttle vector can replicate in *E. coli*. Such shuttle vectors would have high applicability, since *E. coli* is known to be an efficient host for DNA amplification and manipulation.

The plasmids or vectors of the invention can also comprise selective marker genes to allow selection of host cells that have been transformed with a plasmid or a vector. These marker genes encode a protein necessary for the survival or growth of transformed host cells grown in selective culture medium. Host cells not transformed with the vector containing the selection gene will not survive in the culture medium. Typical selection genes encode proteins that confer resistance to antibiotics or other toxins, such as erythromycin, clindamycin, ampicillin, neomycin, kanamycin, penicillin, cetoxifin, imiprenen, metronidazole, streptomycin, chloramphenicol, or tetracycline. Marker genes that are particularly useful in selection of transformed *F. nucleatum* include, e.g., a gene that encodes resistance to clindamycin. Alternatively, selective markers may encode proteins that complement auxotrophic deficiencies or supply critical nutrients not available from complex media. A number of selective markers are known to those skilled in the art and are described for instance in Sambrook et al., supra.

In some embodiments, one or more transcription cassettes comprising a nucleic acid of interest and control sequences can be included to provide an expression vector of the invention. Commonly used control sequences include promoters for transcription initiation, optionally with an operator, along with ribosome binding site sequences. These control sequences are operably linked to a nucleic acid of interest to enable transcription and translation of a polypeptide of interest.

As a promoter, either constitutive or regulated promoters can be used in the present invention, and the selection of a promoter depends on the host cell selected for expression. For example, expression of a nucleic acid of interest in *E. coli* would require a promoter that is functional in *E. coli*. A number of suitable promoters for *E. coli* are known in the art (see, e.g., Sambrook et al., supra). If expression of a nucleic acid in *F. nucleatum* is desired, a promoter that is functional in *F. nucleatum* is included in a plasmid or a vector of the invention. Such promoters can be obtained from genes that have been cloned from *F. nucleatum*, or heterologous promoters functional in *F. nucleatum* may be used. Exemplary genes that have been cloned from *F. nucleatum* include, e.g., afomA gene (see, Haake & Wang, *Archs. Oral Biol.* 42:19–24 (1997)), a fipA gene (see, Demuth et al., *Infec. Immun.* 64:1335–1341 (1996)), etc. The promoters for these genes can be used to express a nucleic acid of interest in *F. nucleatum*.

A ribosome binding site (RBS) can also be included in the transcription cassettes of the invention. An RBS in *E. coli*, for example, consists of 3–9 nucleotides in length located 3–11 nucleotides upstream of the initiation codon (Shine & Dalgarno, *Nature* 254:34 (1975); Steitz, *In Biological Regulation and Development: Gene Expression* (ed. R. F. Goldberger), vol. 1, p.349, Plenum Publishing, NY (1979)).

A nucleic acid of interest in a transcription cassette can include either *F. nucleatum* nucleic acids or foreign nucleic acids. For example, *F. nucleatum* nucleic acids that encode immunosuppressant proteins, such as fomA, fipA, or subsequences thereof, can be included in a transcription cassette. Alternatively, a number of variety of foreign genes can be included in a transcription cassette. For example, leukotoxin genes, such as ltxA, from *Actinobacillus actinomycetemcomitans*, etc., or subsequences thereof can be included in a transcription cassette. In another example, protease genes from *Porphymonas gingivalas*, such as rgpA, rgpB, kgp, prtT, etc., or subsequences thereof can be included in a transcription cassette. In yet another example, cholera toxin genes, such as ctxA, ctxB, or any subunits of cholera toxins, or subsequences thereof can be included in a transcription cassette. If a foreign gene is isolated from a pathogenic microorganism (e.g., a leukotoxin, endotoxin, a cholera toxin, etc.), *F. nucleatum* transformed with such foreign genes or antigenic fragments thereof can be used as a vaccine delivery system to stimulate mucosal immunity against those pathogenic microorganisms.

The nucleic acids of interest can be expressed intracellularly or can be secreted from the cell. Intracellular expression often results in high yields. If necessary, the amount of soluble polypeptides of interest can be increased by performing refolding procedures (see, e.g., Sambrook et al., supra; Marston et al., *Bio/Technology* 2:800 (1984); Schoner et al., *Bio/Technology* 3:151 (1985)). In embodiments in which the polypeptides of interest are secreted from the cell, either into the periplasm or into the extracellular medium, the nucleic acid of interest is linked to another nucleic acid that encodes a cleavable signal peptide sequence. The signal sequence directs translocation of the polypeptide of interest through the cell membrane.

The polypeptides of interest can also be produced as fusion proteins to aid purification of the polypeptides. For example, the DNA encoding the polypeptide of interest may be fused with a nucleotide sequence that contains an affinity tag so that purification of recombinant polypeptides can be simplified. For example, multiple histidine residues encoded by the tag allow the use of metal chelate affinity chromatography methods for the purification of fusion polypeptides. Other examples of affinity tag molecules include, Strep-tag, Pinpoint, maltose binding protein, glutathione S-transferase, etc. See, e.g., Glick and Pasternak, *Molecular Biotechnology Principles and Applications of Recombinant DNA*, 2nd Ed., American Society for Microbiology, Washington, D.C. (1999).

Construction of suitable plasmids or vectors containing one or more of the above listed components employs standard ligation techniques as described in the reference cited above. Isolated plasmids or DNA fragments are cleaved, tailored, and religated in the form desired to generate the plasmids or vectors desired. To confirm correct sequences in a plasmid or a vector constructed, the plasmid or the vector can be analyzed by standard techniques such as by restriction endonuclease digestion, and/or sequencing according to known methods.

VI. Host Cells, Transformation of Host Cells and Protein Purification

A number of host cells can be used for transformation with the vectors of the invention. Examples of useful host cells include *Fusobacterium, Eschericia, Leptotrichia, Streptococcus, Staphylococcus, Clostridium*, etc. Suitable *Fusobacterium* hosts include *F. nucleatum, F. necrophorum, F. varium, F. periodonticum*, etc. In particular, *F. nucleatum* is a preferred host cell. Suitable *F. nucleatum* strains include, e.g., *F. nucleatum* strains 12230 or 10113 (both of which are a gift from S. Finegold, West Los Angeles, Va.), *F. nucleatum* having ATCC Accession Nos. 10953 or 23726, etc. Suitable *Eschericia* hosts include the following strains: JM101, RR1, DH5α, and others. These examples are illustrative rather than limiting.

The host bacterial cells can be transformed with the vectors of the present invention using standard methods appropriate to such cells. These methods include, e.g., electroporation, calcium chloride methods, polyethylene glycol methods, etc. Cells transformed by the vectors can be selected by, e.g., resistance to antibiotics conferred by genes contained on the vector.

For host cells that are transformed with an expression vector, the polypeptides that are expressed by the host cells can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)).

EXAMPLES

The following examples are provided by way of illustration only and not by way of limitation. Those of skill in the art will readily recognize a variety of noncritical parameters that could be changed or modified to yield essentially similar results.

The relevant characteristics of the bacterial strains and plasmids used in the examples below are summarized in Table 4.

TABLE 4

| Bacterial strain Or plasmid | Relevant characteristics[1] | Source/Reference |
|---|---|---|
| E. coli DH5α | Ery$^s$ | Life Technologies, Gaithesburg, MD |
| F. nucleatum 12230 | Cln$^s$, transtracheal isolate, source of pFN1 | S. Finegold, Wadsworth Anaerobe Lab, West Los Angeles VA Medical Center, Los Angeles, CA |
| F. nucleatum 10113 | Clns, clinical isolate, source of pFN2 | S. Finegold, Wadsworth Anaerobe Lab, West Los Angeles VA Medical Center, Los Angeles, CA (strain available as strain deposit number PTA 5816 from the American Type Culture Collection (ATCC), 10801 University Blvd, Manassas, VA 20110-2209). |
| F. nucleatum ATCC 23726 | | American Type Culture Collections, Rockville, MD |
| pBluescript SK(−) | Amp$^r$, 3.0 kb E. coli vector | Stratagene Cloning Systems |
| pVA2198 | Ery$^r$, 9.2 kb plasmid with the ermF-ermAM cassette | F. Macrina (see, Fletcher et al., Infect. Immun. 63:1521–1528 (1995) |

TABLE 4-continued

| Bacterial strain Or plasmid | Relevant characteristics[1] | Source/Reference |
|---|---|---|
| pFN1 | Cln$^s$, 5.9 kb native F. nucleatum plasmid | This study |
| pFN2 | Cln$^s$, 7.2 kb native F. nucleatum plasmic | This study |
| pFN3 | Cln$^s$, 11.1 kb native F. nucleatum plasmid | This study |
| pHS17 | Amp$^r$, Ery$^r$, 10.0 kb plasmid consisting pFN1, ermF-ermAM, and pBluescript minus its ampicillin resistance determinant | This study |
| pHS19 | Amp$^s$, Ery$^r$, 4.1 kb plasmid consisting of ermF-ermAM and pBluescript minus its ampicillin resistance determinant | This study |

[1]Abbreviations: amp, ampicillin; ery, erythromycin; cln, clindamycin.

Example 1

Isolation and Characterization of *F. nucleatum* Plasmids

Three native plasmids pFN1, pFN2, and pFN3 (see, e.g.,Table 1; FIG. 1A) were isolated from strains of *F. nucleatum* using routine techniques (Wizard Plus Minipreps; Promega, Madison, Wis.; Qiagen Midi Preps, Qiagen Inc., Valencia, Calif.) and visualized on ethidium-stained 0.8% agarose gels. Restriction endonuclease mapping was accomplished using standard recombinant DNA technologies (see, Kinder Haake et al., *Arch. Oral Biol.* 42:19–24 (1997)). The results of restriction endonuclease mapping demonstrated that the plasmids varied in size and in the occurrence of several restriction endonuclease sites (see, FIG. 1A), suggesting that the plasmids were unrelated.

Figure 1B:
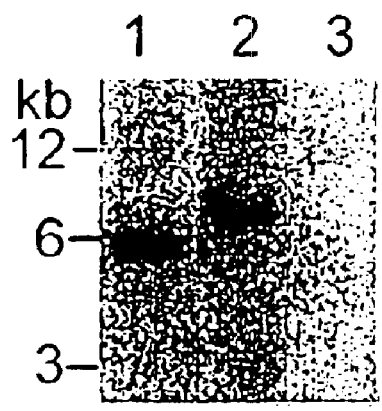
FIG. 1B and FIG. 1C show Southern blots of *F. nucleatum* plasmids. Plasmids from *F. nucleatum* strains 12230 (PFN1, lanes 1), 10113 (pFN2, lanes 2) and ATCC 10953 (pFN3, lanes 3) were probed with pFN1 (panel B; EcoRI digests) or pFN3 (panel C; EcoRV digests) DNA. The HincII-digested pFN1 and AseI-digested pFN3 probes were $^{32}$P-labeled (specific activity of 25 and $4.5 \times 10^8$ dpm/μg DNA, respectively). The positions of molecular size markers are indicated on the left, and the linear form of pFN1, pFN2 and pFN3 are indicated on the right.
Figure 1C:
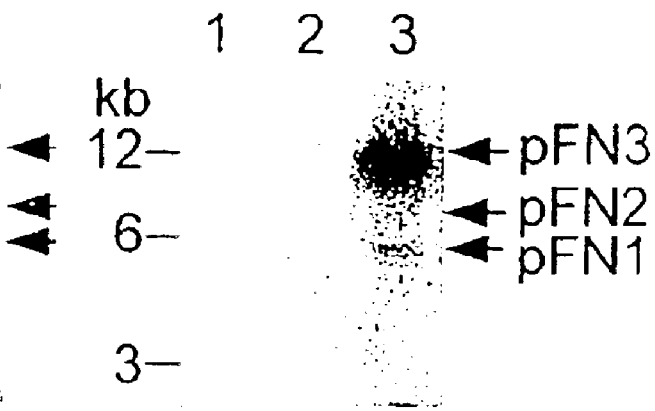

Southern hybridization studies were performed under conditions described in Kinder et al., *Gene* 136:271–275 (1993), and the results indicated that pFN1 and pFN2 share homology with each other, but not with pFN3 (see, FIGS. 1B-C). Nitrocellulose blots of plasmid and chromosomal DNA preparations from the plasmid-containing host strains were probed with pFN1 and pFN3 DNA. The pFN1-probe hybridized to pFN1 and pFN2, but not pFN3 DNA (see, FIG. 1B), whereas the pFN3-probe hybridized only to pFN3 (see, FIG. 1C). No hybridization to chromosomal DNA from any of the host strains was evident (data not shown).

The strain harboring pFN3, ATCC 10953, was previously reported to lack plasmid DNA (see, McKay et al., *Plasmid* 33:15–20 (1995)). Due to this discrepancy we obtained a new culture from ATCC and confirmed the presence of pFN3 in this strain. These data reveal the existence of two non-homologous groups of plasmids indigenous to *F. nucleatum*, the first represented by pFN1 and pFN2, and the second represented by pFN3.

Example 2

Figure 2A:
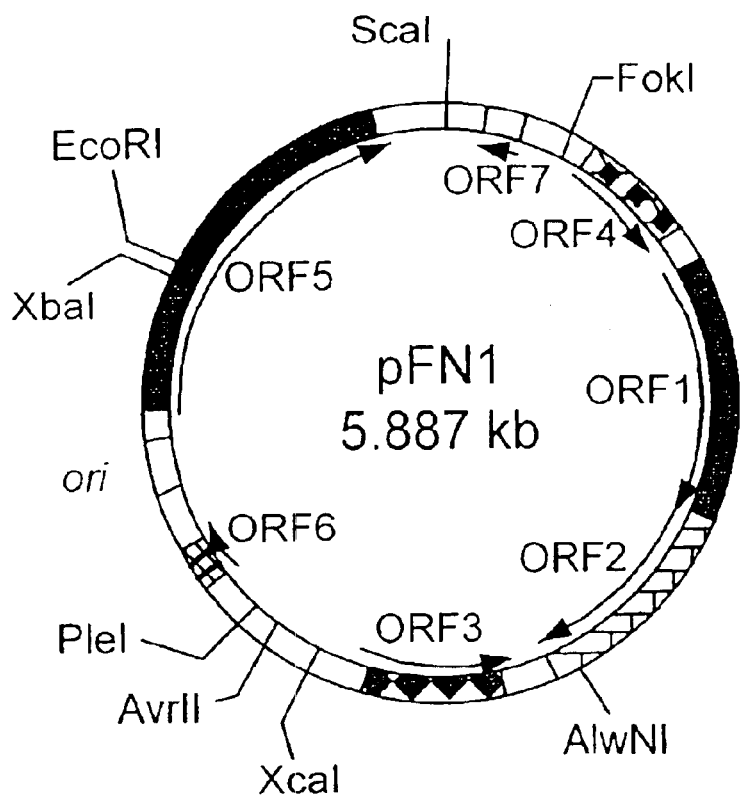
FIG. 2A shows physical characteristics of plasmid pFN1 based on DNA sequence analysis. Open reading frames (ORFs), the putative origin of replication (ori), and selected restriction endonuclease sites are indicated.

Determination and Analysis of pFN1 DNA Sequence and Partial pFN3 DNA Sequence Due to its small size and superior plasmid yields, pFN1 was chosen for further analysis. The DNA sequence (GenBank Accession No. AF159249) was determined for both strands. Analysis of the compiled sequence revealed a circular structure of 5887 bp with 23% G+C content and seven putative open reading frames (ORFs defined as ≧150 bp; FIG. 2A). Similarity searches were performed using the National Center for Biotechnology Information BLAST server (Altschul et al., *J. Mol. Biol.* 215:403–410 (1990); Altschul et al., *Nuc. Acids Res.* 25:3389–3402 (1997)). The sequence of pFN1 was highly homologous to the sequence of a 6281 bp *F. nucleatum* plasmid (pAD52, GenBank Accession No. AF022647). No similarity was found to any gene encoding antibiotic resistance or other selectable phenotypic marker. Antibiotic susceptibility testing indicated that the pFN1 host strain *F. nucleatum* 12230 was susceptible to penicillin G, tetracycline, chloramphenicol, clindamycin, cetoxifin, ampicillin/sulbactam, imipenem, metronidazole and streptomycin, and resistant to erythromycin at 25 $\mu$g/ml as is common in *F. nucleatum* (see, Brazier et al., *J. Appl. Bacteriol.* 71:343–346 (1991)). These data suggested that pFN1 is a cryptic plasmid with respect to antibiotic resistance, comparable to previous findings with this group of plasmids (see, McKay et al., *Plasmid* 33:15–20 (1995)).

ORF1 is related to DNA relaxase (mobilization) proteins which mediate the initiation of conjugal transfer of plasmid DNA (Ilyina et al., *Nuc. Acids Res.* 20:3279–3285 (1992)). Alignment of the complete predicted amino acid sequences using Clustal W (Higgins, *Methods Mol. Biol.* 25:307–318 (1994); Thompson et al., *Nuc. Acids Res.* 22:4673–4680 (1994)) of ORF1 with *Staphylococcus* plasmid relaxases demonstrated 23 to 29% identity and 30 to 34% similarity. Homology to the four regions of the consensus sequence defined for relaxase proteins (Ilyina et al., supra) was evident (data not shown).

Figure 2B:
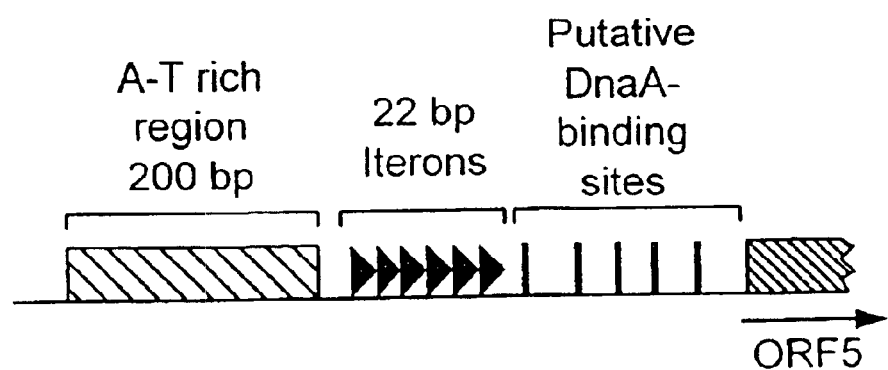
FIG. 2B shows structural elements of putative origin of replication found upstream of ORF5, the repA homologue. The putative origin contains an A-T rich region (cross hatched bar), six perfect 22 bp direct repeats (▲) termed iterons, and several putative DnaA-binding sites (■).

ORF5 analyses indicated that it is related to plasmid replication proteins, including *Lactobacillus acidophilus* plasmid pLA103 (Kanatani et al., *FEMS Microbiol Lett.* 133:127–130 (1995)), *Staphylococcus aureus* plasmid pJE1 (Berg et al., *J. Bacteriol.* 180:4350–4359 (1998)), and *Pediococcus halophilus* pUCL287 (Benachour et al., *FEMS Microbiol. Lett.* 128:167–176 (1995)). Alignment of the complete ORFs of homologues with pFN1 ORF5 demonstrated 10 to 19% identity and 21 to 34% similarity. The association of ORF5 with replication was strongly supported by analyses of the upstream DNA sequence, which demonstrated six perfect 22 bp direct repeats ("iterons") preceded by an approximately 200 bp A-T rich region (FIG. 2B). Multiple putative DnaA binding sites were also identified, based on matching eight of the nine bp comprising the DnaA binding consensus sequence (Schaefer et al., *Mol. Gen. Genet.* 226:34–40 (1991)). This organization is characteristic of the origin of replication of iteron-regulated theta-replicating plasmids (Helinski et al., Replication control and other stable maintenance mechanisms of plasmids, p. 2295–2324. In Neidhardt (ed.), *Escherichia coli* and *Salmonella,* 2nd ed., vol. 2. ASM Press, Washington, D.C. (1996)). A general model of replication initiation involves the binding of the plasmid replication protein to the iteron sequences resulting in structural changes, including melting of the adjacent A-T rich region, to form an open complex. The replication protein, possibly in conjunction with the host DnaA protein, is then responsible for guiding host replication proteins into the open complex (Helinski, et al., supra; Neidhardt, supra). It is also significant that the pFN1 replication protein homologue was related to the replication protein of pUCL287, which has been shown to utilize a theta mode of replication (Benachour et al., *FEMS Microbiol. Lett.* 128:167–176 (1995)).

A partial DNA sequencing was also performed with plasmid pFN3. The partial nucleotide sequence of plasmid pFN3 is as shown in SEQ ID NO:14. The sequence is degenerate in that there were ambiguous bases (designated as "N") within the sequence. The sequence analysis was performed using a clone of a fragment of plasmid pFN3 (clone designated as pSY1).

Example 3

Homology Studies Between Plasmids pFN1 and pFN2

To further characterize the regions of homology between pFN2 and pFN1, a Southern blot analysis was done using probes specific for two pFN1 genes. Plasmids pFN1 and pFN2 were subject to restriction endonuclease digestion using different restriction endonucleases and then electrophoresis on 0.8% agarose gel. The DNA was transferred to nitrocellulose, hybridized with the radiolabeled probe, and washed according to standard techniques (see, Kinder et al., *Gene* 136:271–5 (1993)). Partial restriction maps are as shown in FIG. 3. As evident in FIG. 3, different restriction endonucleases were used for these homology studies.

The repA and rlx gene sequences were amplified from pFN1 DNA using the polymerase chain reaction with oligonucleotide primers specific for these regions. The DNA probes used were amplified by polymerase chain reaction from pFN1 using custom primers (rlx primers: 5'-CCTGG TGAAGTAGATGAAG-3' (SEQ ID NO:7), 5'-TTAGTTTTAGCAATGGAAG-3' (SEQ ID NO:8), repA primers: 5'-ATGCTGGAGTGTGATATG-3' (SEQ ID NO:9), 5'-GTTGATTTTCCACTTTCGG-3' (SEQ ID NO:10); Gibco Life Technologies, Grand Island, N.Y.).

Figures 4A, 4B, 4C:
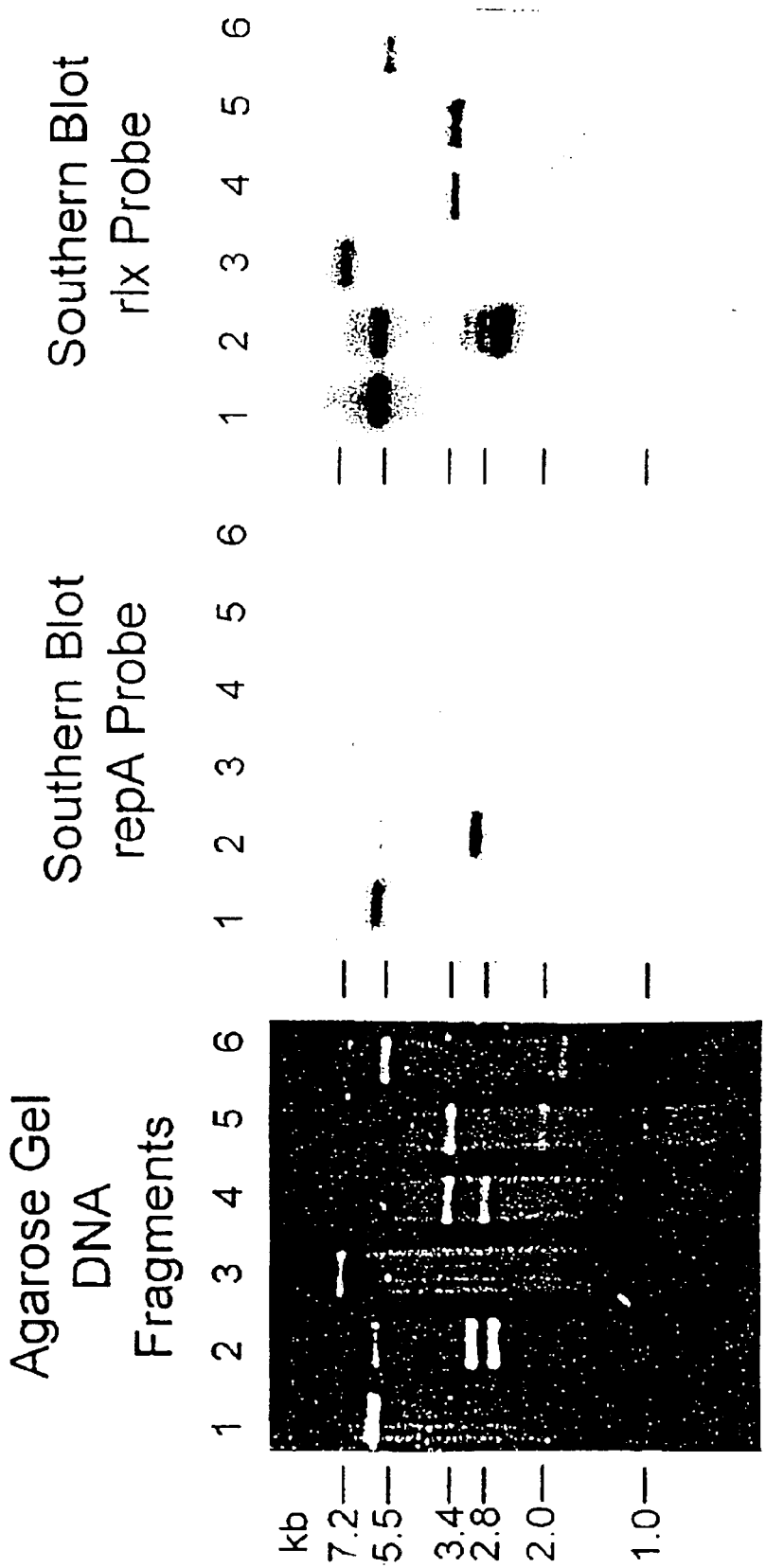
FIGS. 4A–C shows Southern blot analysis of pFN1 and pFN2 DNA with the pFN1 repA and rlx gene probes. The left panel (Panel A) shows agarose gel demonstrating restriction endonuclease digestion fragments of pFN1 and pFN2 DNA. The middle panel (Panel B) shows Southern blot of pFN1 and pFN2 DNA with pFN1 repA gene probe. The right panel (Panel C) shows Southern blot of pFN1 and pFN2 DNA with pFN1 rlx gene probe. For all panels: lane 1, EcoRI digested pFN1 lane 2, StyI digested pFN1; lane 3, EcoRI digested pFN2; lane 4, HincII digested pFN2; lane 5, HincII/HpaI digested pFN2; lane 6, AvrII digested pFN2.

Hybridization of the repA and rlx probes with pFN1 digests gave the expected results (FIG. 4, lanes 1 and 2; FIG. 5). Both probes hybridized with the linear 5.9 kb pFN1 DNA band (FIG. 4, lanes 1). The repA probe hybridized to the 3.1 kb band of the pFN1 StyI digested DNA (FIG. 4, lane 2, left and middle panels) whereas the rlx probe hybridized to the 2.7 kb band (FIG. 4, lane 2, left and right panel).

Hybridization of both the pFN1 repA and rlx gene probes were evident with the linear pFN2 band at 7.2 kb (FIG. 4, lane 3, middle and right panels). The pFN1 repA probe (FIG. 4, middle panel) hybridized with a 2.8 kb band in the HincII digest (lane 4), a 0.9 kb band in the HincII/HpaII digest (lane 5), and a 5.5 kb band in the AvrII digest (lane 6). This pattern of hybridization indicates that the region of homology of the pFN1 repA gene on pFN2 is localized to the 0.9 kb HincII/HpaII fragment (FIG. 5).

The pFN1 rlx gene probe (FIG. 4, right panel) demonstrated hybridization with the 3.4 kb bands in the HincII (lane 4) and HincII/HpaII (lane 5) digests, and with a 5.5 kb band in the AvrII digest (lane 6). These data indicate that the region with homology to the pFN1 rlx gene is localized to the 2.2 kb HincII-AvrII fragments of pFN2 (FIG. 5).

Example 4

Isolation of repA Nucleic Acids and Origin of Replication Sequences

The repA nucleic acids and origin of replication sequences of the invention can be obtained using a number of methods known in the art. This example illustrates the isolation of repA nucleic acids and origin of replication sequences using PCR methods. PCR reactions are performed as described by the manufacturer (e.g., Boehringer Mannheim, Montreal). The primers used to amplify the repA and origin of replication sequences were based on the sequence information of plasmid pFN1 (see, SEQ ID NO:6).

To amplify repA gene sequence (pFN1 nucleotide positions 4429 to 158 [note that this goes through the "0" position]), the following primers can be used.

Forward: 5'-GAC ATT AAG TGA AAA AG-3' (SEQ ID NO:16)

Reverse: 5'-ATG CTG GAG TGT GAT ATG-3' (SEQ ID NO:17)

To amplify the origin of replication, including the AT rich region, the iteron repeat sequences and the putative DnaA binding sites (positions 3677 to 4487 of pFN1), the following primer can be used.

Forward: 5'-ACG GAT ACT TTG TTG CT-3' (SEQ ID NO:18)

Reverse: 5'-TAT CCT TTA CAT TTA-3' (SEQ ID NO:19)

To amplify the origin of replication and the repA gene, combined (PFN1 nucleotide positions 3677 to 158 [note that this sequence goes through the "0" position]), the following primer can be used.

Forward: 5'-ACG GAT ACT TTG TTG CT-3' (SEQ ID NOS:20)

Reverse: 5'-ATG CTG GAG TGT GAT ATG-3' (SEQ ID NO:21)

The PCR products are purified on a spin column (e.g., S-300 spin column; Pharmacia Biotech) and are sequenced to confirm isolation of the correct sequences.

Example 5

Transformation of *F. nucleatum* with the Shuttle Plasmid pHS17

The shuttle plasmid pHS17 (FIG. 1A) was constructed sequentially in *F. coli* DHα cells (Life Technologies, Gaithersburg, Md.) as follows: AvrII-digested pFN1 was cloned into the XbaI site of pBluescript; an ermF-ermAM cassette (Fletcher et al., *Infect. Immun.* 63:1521–1528 (1995); see also, GenBank Acc. No. AF219231) was added by cloning into KpnI/PstI sites; and the pBluescript ampicillin resistance determinant was deleted by digestion with flanking BspHI sites. The resulting construct included both *E. coli* and *F. nucleatum* origins of replication, from pBluescript and pFN1, respectively. The junctions of DNA fragments joined by cloning were confirmed by DNA sequencing, and the phenotypic properties of the construct were confirmed on selective media.

Transformation studies were performed with plasmid DNA isolated by alkaline lysis/column purification techniques (Wizard Plus Minipreps, Promega, Madison, Wis.; Qiagen Midi Preps, Qiagen Inc. Valencia, Calif.) and further purified by cesium chloride ethidium bromide density gradient centrifugation (see, Sambrook, supra). Bacterial cells were washed, resuspended in electroporation buffer according to methods of Fletcher et al., supra, at a calculated optical density of 0.60. 100 µl aliquots were electroporated using standard techniques (see, Sreenivasan et al., *Infect. Immun.* 59:4621–4627 (1991)). The electroporated cells were immediately diluted with 0.9 ml of Columbia broth (BBL Microbiology Systems, Cockeysville, Md.) with $MgCl_2$, and the number of viable cells were determined by plating a diluted aliquot on non-selective media. The transformation mix was incubated anaerobically followed by plating on Columbia agar (BBL Microbiology Systems) with clindamycin. Variables examined included the bacterial cell growth phase (early log, mid-log, and stationary phase), the source of pHS 17 DNA (heterologous versus homologous host sources), electroporation parameters (resistance of 50 to 500 Ω; field strength of 24 or 25 kV/cm; capacitance of 25 or 50 µF), the concentration of $MgCl_2$, in the Columbia broth (0.5, 1.0, 2.0 mM), and the clindamycin concentration used in the selective media (0.2 or 0.4 µg/ml).

Figure 6:
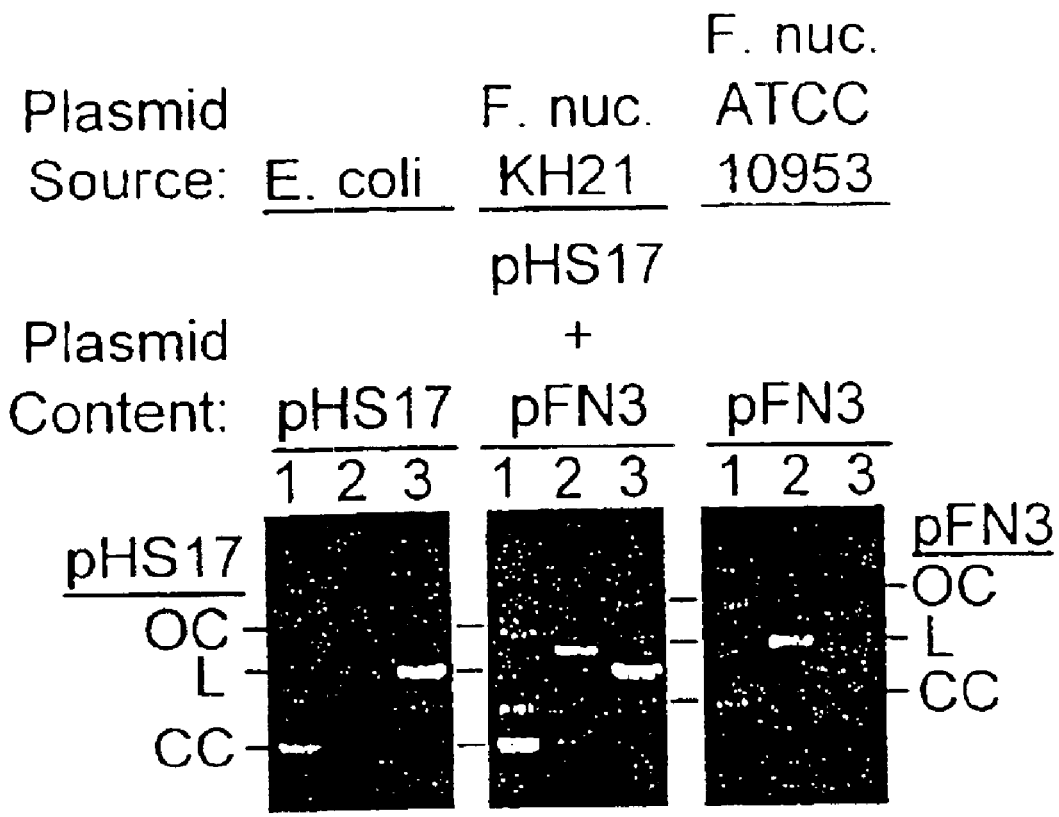
FIG. 6 shows that plasmid DNA from *F. nucleatum* ATCC 10953 transformants consists of the shuttle plasmid, pHS 17, and the native plasmid, pFN3. Plasmid preparations from *E. coli* (pHS17), *F. nucleatum* ATCC 10953 transformant strain KH21 (pHS17 and pFN3) and *F. nucleatum* ATCC 10953 (pFN3) were analyzed. The preparations were not digested (lanes 1), or predigested with EcoRV (lanes 2) or EcoRI (lanes 3), separated on 0.8% agarose gels, stained with ethidium bromide and visualized under UV illumination. The open circular (OC), linear (L) and covalently closed circular (CC) forms of pHS17 and pFN3 are indicated on the left and right, respectively.

Transformation of *F. nucleatum* ATCC 10953 with pHS17 were successful using previously defined conditions (Fletcher, *Appl. Environ. Microbiol.* 52:672–676 (1986); Rosey et al., *J. Bacteriol.* 177: 5959–5970 (1995); Sreenivasan et al., supra). Preliminary results indicated optimal recovery of transformant with a field strength of 25 kV/cm, a capacitance of 25 µF, and resistance ranging from 200 to 400 Ω. Analysis of the transformants revealed the presence of pHS17, and the ATCC 10953 native plasmid pFN3. The two plasmids were easily distinguished based on their sizes and restriction endonuclease digestion patterns (FIG. 6). Electroporation controls included non-electroporated cells with or without the addition of DNA as well as electroporated cells without DNA added, and all yielded negative results. Electroporation with pHS19 also yielded negative results, suggesting that pFN1 is essential for replication in *F. nucleatum*.

Transformation efficiency was dependent on the pHS 17 DNA source. The transformation efficiency using 1 µg of plasmid DNA ranged from 1.6 to $2 \times 10^2$ transformants per µg of DNA from the homologous *F. nucleatum* host, as compared to no transformants with DNA from the heterologous *E. coli* host as shown in Table 4 below.

TABLE 4

| | Resistance[b] | Heterologous plasmid DNA[a]: pHS17 | | Homologous plasmid DNA[a]: pHS17 + pFN3 |
|---|---|---|---|---|
| | (Ohms): | 1 µg DNA | 5 µg DNA | 1 µg DNA |
| Transformation Efficiency[c] | 400 | 0 | $1.2 \times 10^1$ | $1.6 \times 10^2$ |
| | 300 | 0 | 0 | $1.9 \times 10^2$ |
| | 200 | 0 | 1 | $2.0 \times 10^2$ |

[a]Heterologous plasmid DNA was isolated from *E. coli* strain KTK5 (pHS17). Homologous plasmid DNA was isolated from *F. nucleatum* strain KH21 (pHS17, pFN3). The quantitation of plasmid DNA is based on total DNA in the preparation.
[b]See above for additional electroporation parameters. Outgrowth period was approximately 12 hours.
[c]Calculated as the number of transformants per ml/number of µg of DNA (see, Sreenivasan et al., Infect. Immun. 59(12):4621–4627). The average cells remaining after electroporation at 400, 300 and 200 ohms was $0.39 \times 10^8$, $1.1 \times 10^8$ and $2.1 \times 10^8$, respectively.

Transformation efficiency was optimal at a resistance setting of 200 Ω using the homologous host DNA, although pronounced difference were not evident over the range examined. Transformation with *E. coli* pHS17 DNA at 5 µg was demonstrated; however, the efficiency was still less than that observed with 1 µg of homologous DNA The 100-fold or greater increase in transformation efficiency with homologous DNA suggests the presence of a functional restriction-modification system in *F. nucleatum* ATCC 10953. Restriction-modification systems in *F. nucleatum* have been previously reported (see, Leung et al., *Nuc. Acids Res.* 6:17–25 (1979); Lui et al., *Nuc. Acids Res.* 6:1–15 (1979)).

Growth phase also influenced the transformation efficiency, but to a lesser extent than the DNA source.

Increased transformation efficiencies were transformation efficiencies were routinely obtained with early log phase cells. For example, in one experiment using early log, mid-log and stationary phase recipient cells and an outgrowth period of 5 hours (approximately 2 generations), the transformation efficiencies were 7.2, 4.8 and 5.0×10$^3$, respectively. No significant differences were observed with variations in the concentration of MgCl$_2$ in the outgrowth broth, or with 0.2 versus 0.4 μg/ml clindamycin in the selective agar media.

In addition, *F. nucleatum* subspecies *nucleatum* ATCC 23726 yielded transformants with an efficiency ranging from 1.2×10$^4$ transformants per ml per μg of DNA. Analyses revealed the presence of plasmid DNA from the transformants that was consistent with pHS17 in size and restriction endonuclease digestion pattern.

Example 6

Stability of Shuttle Plasmid in *F. nucleatum* Transformants

The structural stability of pHS17 in representative transformants was evaluated by restriction endonuclease mapping, PCR-amplification of pHS17-specific DNA regions, and Southern analysis of the transformant DNA with pFN1 and pHS17 DNA probes (data not shown). In all of the analyses done, no evidence of DNA rearrangement or deletion was detected. The segregational stability of pHS17 was examined in the transformant strain KH21 maintained in liquid cultures without antibiotic selection as described in Roberts et al., *J. Bacteriol.* 174:8119–8132 (1992). After 100 generations the percentage loss of plasmid per generation was 0.02, with an average of 98% of the viable cells demonstrating the clindamycin-resistance phenotype. The shuttle plasmid was present in all colonies subcultured at baseline and after 100 generations, with no evidence of DNA rearrangement or deletion. Thus, pHS17 was found to be both structurally and segregationally stable in the *F. nucleatum* host cell background. Interestingly, both pHS17 and pFN3 were stably maintained in the transformants, indicating that these two plasmids are compatible, and that pFN3 may be useful in developing plasmid vectors for use in conjunction with pFN1-derived plasmids.

The present invention provides novel materials and methods related to *Fusobacterium*. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit any particular reference is "prior art" to their invention.

---

SEQUENCE LISTING

<160> NUMBER OF SEQ ID NOS: 21

<210> SEQ ID NO 1
<211> LENGTH: 407
<212> TYPE: PRT
<213> ORGANISM: Fusobacterium nucleatum
<220> FEATURE:
<223> OTHER INFORMATION: RepA

<400> SEQUENCE: 1

```
Met Asp Phe Ser Ser Ile Lys Lys Ser Leu Gly Leu Ile Asn Phe Arg
 1               5                  10                  15

Asp Leu Lys Lys Tyr Ile Leu Gly Leu His Gln Lys Leu Gly Asn Leu
            20                  25                  30

His Ile Thr Asn Ile Thr Asn Lys Lys Ile Glu Thr Ile Phe Leu Phe
        35                  40                  45

Glu Lys Phe Ile Asn Asp Leu Asp Asn Asn Thr Leu Thr Ile Arg Val
    50                  55                  60

Thr Lys Asp Ser Leu Tyr Phe Phe Asn Ile Ala Asn Ser Tyr Leu Arg
65                  70                  75                  80

Phe Leu Phe Ser Asp Val Arg Lys Leu Ser Gly Lys Tyr Ser Lys Leu
                85                  90                  95

Leu Val Pro Tyr Leu Met Glu Phe Ser His Lys Lys Glu Ala Glu Phe
            100                 105                 110

Glu Lys Glu Arg Phe Phe Asn Ile Leu Glu Val Glu Glu Ser Tyr Arg
        115                 120                 125
```

```
Asn Asn Leu Ser Asp Phe Asn Lys Arg Ile Leu Lys Pro Ala Val Glu
        130                 135                 140

Glu Leu Lys Thr Leu Phe Glu Asn Leu Lys Val Glu Arg Leu Lys Asn
145                 150                 155                 160

Gly Arg Val Ile Lys Gly Tyr Lys Phe Ser Trp Thr Asn Asp Phe Asn
                165                 170                 175

Phe Gln Asn Lys Lys Asp Asn Ile Glu Glu Ala Glu Val Val Glu Glu
            180                 185                 190

Lys Glu Asn Ile Ala Ser Gly Glu Leu Glu Lys Tyr Phe Lys Ser Thr
        195                 200                 205

Phe Thr Asp Val Asn Tyr Ser Lys Lys His Lys Glu Val Leu Glu Lys
    210                 215                 220

Leu Leu Lys Asn Asn Ser Leu Glu Tyr Ile Lys Lys Tyr Leu Ser Glu
225                 230                 235                 240

Gln Trp Glu Tyr Val Gln Asn Asp Lys Asn Ile Leu Asn Lys Ser Ala
                245                 250                 255

Tyr Phe Ser Lys Leu Ile Leu Glu Glu Lys Ala Val Tyr Lys Asn His
            260                 265                 270

Leu Pro Ala Asp Tyr Glu Glu Leu Lys Val Glu Glu Arg Asn Arg Asn
        275                 280                 285

Ile Glu Ser Thr Asn Thr Ile Thr Ser Leu Lys Asp Leu Val Glu Lys
    290                 295                 300

Asp Ile Thr Asp Tyr Glu Val Arg Lys Asn Ile Thr Pro Glu Gln Ile
305                 310                 315                 320

Glu Gln Glu Val Leu Phe Lys Ile Asp Val Thr Glu Glu Tyr Asn
                325                 330                 335

Lys Ile Lys Glu Asp Trp Ile Ile Lys Arg Lys Asp Glu Val Pro Asn
            340                 345                 350

Ser Asp Pro Lys Leu Leu Glu Ile Ile Phe Asn Ala Ser Gln Ser Lys
        355                 360                 365

Lys Tyr Asn Ile Ile Asn Thr Lys Glu Glu Val Asn Glu Lys Glu Lys
    370                 375                 380

Glu Leu His Glu Leu Glu Glu Asn Ile Lys Arg Met Gln Glu Glu Leu
385                 390                 395                 400

Asn Lys Leu Lys Lys Glu Val
                405

<210> SEQ ID NO 2
<211> LENGTH: 1224
<212> TYPE: DNA
<213> ORGANISM: Fusobacterium nucleatum
<220> FEATURE:
<223> OTHER INFORMATION: repA

<400> SEQUENCE: 2
atggattttt cttctataaa aaaaagttta ggtttaatta attttagaga tttaaaaaaa      60
tatattttag gacttcatca aaaattagga aatttacata ttactaatat aacaaataaa     120
aaaattgaaa caatcttttt atttgaaaaa ttcataaatg atttagataa taatacttta     180
actataagag taacaaaaga ttctctttat tttttttaata ttgctaacag ttatttaagg    240
tttctctttt cagatgttag aaaactttca ggaaaatatt caaagttatt ggttccttat     300
ttaatggagt ttagtcataa aaaagaagct gaatttgaaa agagagatt ttttaatatt     360 ctagaagttg aagaaagtta tagaaataat ttatcagatt ttaataagag aattctaaaa    420
```

-continued

```
ccagctgttg aagaattaaa aacactttttt gaaaatttaa aggttgagcg attaaaaaat    480
ggaagagtaa taaaaggata taaatttagc tggactaatg atttttaattt tcaaaataag    540 aaagataata tagaagaagc agaagtagtg gaagaaaaag aaaatattgc ttcaggagag    600
ttagaaaaat attttaaatc aacttttact gatgtaaatt attcaaagaa gcataaagaa    660
gttttagaaa aattattaaa aaataatagt ttagaatata ttaaaaaata tttatctgag    720
cagtgggagt atgtacaaaa tgataaaaat attttaaata aatcagcata tttctcaaaa    780
ctaattttag aagaaaaagc agtatataaa aatcatctac cagctgacta tgaagaacta    840
aaagttgaag aaagaaatag aaatatagaa agtacaaata ctattacatc attaaaagat    900
ttagtagaaa aagacattac agattatgaa gttagaaaga ataactcc tgaacaaata    960 gaacaagaag tttatttaa aatagatgta actgaagaag aatataataa gattaaagaa   1020
gattggataa taaaacgaaa agatgaagtt cctaatagtg atccaaaact tttagaaatt   1080
atatttaatg caagtcaatc aaaaaaatat aatataatta atactaaaga agaagttaat   1140 gaaaagaaa aagagcttca cgaattagaa gaaaatataa aagaatgca agaagaacta   1200 aataaattaa aaaaagaggt atag                                          1224

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:iteron
      sequence within the origin of replication of plasmid pFN1

<400> SEQUENCE: 3 tcaacttttaa caggacaaat tt                                             22

<210> SEQ ID NO 4
<211> LENGTH: 132
<212> TYPE: DNA
<213> ORGANISM: Artificial Sequence
<220> FEATURE:
<223> OTHER INFORMATION: Description of Artificial Sequence:six copies
      of the iteron sequence within the origin of replication of plasmid
      pFN1

<400> SEQUENCE: 4
tcaactttaa caggacaaat tttcaacttt aacaggacaa attttcaact ttaacaggac     60
aaattttcaa ctttaacagg acaaattttc aactttaaca ggacaaattt tcaactttaa    120
caggacaaat tt                                                        132

<210> SEQ ID NO 5
<211> LENGTH: 1230
<212> TYPE: DNA
<213> ORGANISM: Artificial Sequence
<220> FEATURE:
<223> OTHER INFORMATION: Description of Artificial Sequence:repA homolog
      sequence of plasmid pAD52

<400> SEQUENCE: 5 atggatttt cttctataaa aaaagtttta ggtttaatta attttagaga tttaaaaaaa     60
tatattttag gacttcatca aaaattagga aatttacata ttactaatat aacaaataaa    120
aaaattgaaa caatcttttt atttgaaaaa tcataaatg atttagataa taatactttta    180 actataagag taacaaaaga ttctctttat tttttttaata ttgctaacag ttatttaagg    240
tttctctttt cagatgttag aaaacttttca ggaaaatatt caagttatt ggttcctat    300
```

-continued

```
ttaatggagt ttagtcataa aaagaagct gaatttgaaa aagagagatt ttttaatatt      360
ctagaagttg aagaaagtta tagaaataat ttatcagatt ttaataagag aattctaaaa      420
ccagctgttg aagaattaaa aacacttttt gaaaatttaa aggttgagcg attaaaaaat      480
ggaagagtaa taaaggata taaatttagc tggactaatg atttaattt tcaaaataag      540 aaagataata tagaagaagc agaagtagtg gaagaaaaag aaaataaaaa tattgctcct      600
ggagagttag aaaaatattt taaaacaact ttccctggtg taaattattc aaagaagcat      660
aaagaagttt tagaaaaatt attaaaaaat aatagtttag aatatattaa aaaatatta      720 tctgagcagt gggagtatgt acaaaacgat aaaaatatt taaataaatc agcatatttt      780
tcaaaactaa tcttagaaga aaaagcagta tataaaaatc atctaccagc tgactatgaa      840
gaattaaaag ttgaagaaag aatagaaat atagaaagta caaatactat tacatcatta      900
aaagatttag tagaaaaaga cattacagat tatgaattta gaaagaatat aactcctgaa      960
caaatagaac aagaagtttt atttaaaata gatgtaactg aagaagaata taataagatt     1020
aaagaagatt ggataataaa acaaaaagaa gtagttccta atagtgatcc agaacttta     1080 gaagttatat ttaatgcaag tcaatcaaaa aaatataata taattaatac taagaagaa      1140 gttaatgaaa aagaaaaaga gcttcacgaa ttagaagaaa atataaaaag aatgcaagaa      1200
gaaataaata aattaaaaaa agaggtatag                                      1230
```

<210> SEQ ID NO 6
<211> LENGTH: 5887
<212> TYPE: DNA
<213> ORGANISM: Artificial Sequence
<220> FEATURE:
<223> OTHER INFORMATION: Description of Artificial Sequence:plasmid pFN1

<400> SEQUENCE: 6

```
catataataa cttttgttt ctttcttcta gtactttttt ttctaactct tttaatttct       60
ttttactttt ttcaattttt tctaattcaa tcgcttttaa ttcttctaaa gtcttttta      120 ttttttagt agcttccata catatcacac tccagcatta ttatttataa aaatataatt      180
atatataaca tatctagtaa aataaatcaa gtagtgtcgg cttaaacaag agccatataa      240
attaaaaaat atatatattt ttcttttaat ttctaatata aaatggtata atattttata      300
tggcattgtt taaggcaagc tactcactcc tgccgtcgtg tagcttgctg ggaagtatcc      360
cagaccctca gaagcaccta caaaattaa aaatatattt ttaattttct tcggtactta      420
tagggggatg accccctataa cccctgcgag ttgattttat aaaattcttg cagggacagc      480
tgcaattatt ttataaaacc aactttaaag agagtgataa taatgattaa atttacatta      540
agattaataa taatgattaa atttacatta agattaacgg aagatgaaaa aaaacttta      600 gatataaaag ctgatgaatt aggtaaatca aaaaatgaag ttttaaagtt tcttataaac      660
aataaattgg aagatactaa aaaagaattt gacctattaa atgagcttga taaaaattat      720
aaagagctag gttttcagat taaaaaaatt ggagtagttt taaatcagat taataaaaat      780
ttttatgaag ataagaaaat acagattgaa gaaatccaag gagcgttaga tgaattatgg      840
cagtctataa aagtgtcaaa ggagtaggaa aaactaaaag cagtttatac aatatttttaa      900 agtatgtagg aagtcaaaat gaaaaagaaa agatgatag agtttataaa actactggta      960
taaatgttag tgatgattat aaaaaagctt ttaaagaaat gatgttaaca aaagagcttc     1020
attgtaagtt agacggtaga caatatagac accatatta atcttttaaa cctggtgaag     1080
```

-continued

```
tagatgaaga aacagcacat aaaatggcag tagaatttgc agaaaaaaat tttaaaggct    1140
ttgatgtttt tatatcaact cacattgata aaggacacat acataaccat ataattatta    1200
atactgttaa tattgatact ggaatgaagt tcagagaatt aaataagaat gaatataatc    1260
aaaaaaaaga aaataatgtt gaattaaaat ctcacgaatt ttatttagaa gatttaaaaa    1320
aatctagtga tgaaatttgt cttgcaaata atttatcggt gatcccccaa aaagaaaaag    1380
ctgaaagtca gaatatttat aatagacgag aatataatgt tgtgatgaac aaaacaagtt    1440
ataaaatgga gctggcaaaa gatataaaaa gagcttccaa gaattgtaaa tcaaagaag     1500
atttttataaa agcattagat gaaaaggtg ttattgtgga ttgggaagac cataaaaaac    1560
atataacttt taaatttaaa gatgagaaaa agaaatcaat tagattagca aatttagaaa    1620
aaactttcca agatgaaact tttaaaaagg aatacctgga acagcaattt ttaataaatc    1680
aaaaaactga agaaatagga aatttcaaaa ttaaagttaa tactgaagct gaaaaaacta    1740
atgaagaaaa atatcaagag cttctaaata aaaagagaga acaagataaa ttaatagctg    1800
aagaaaaatt gaaaagcaa aaagaagaaa ttgagaaaaa gaaaaattta aatagaaaca    1860
aaggtttcgg aataggagat taaaaatggc tatattagat gatgatgtaa atgaagttaa    1920
aaatgtgaat gagcaagaaa taaaaatgga tagttatatt aaaaaaataa ttgaaaatgt    1980
tttagaagtt cagctaaaag aacataaaga aatagcttcc attgctaaaa ctaaaatagc    2040
tgaagtaact ttagaactag aaaaattaaa acagctggag aaagcaacta ctaaatatag    2100
agatgataca aatataatta caaataaaat gattgaaaat gttgaaaatt ataataaagt    2160
attttagaa agaattgata aatttaattt attgatggta gaaaagttaa atgaagtaaa    2220
aaatactaat caaatatttg ctgagacatt agataaatca gatattgttg ataaccttaa    2280
taagagtaga gcagaaatat ttgagaaatt ttcaactgat gttgctacaa aaacaaataa    2340
tactttaat ttaattgaag atagtctaaa taaattaaaa atagccttct atacagctgt    2400
atctgttatt gtaatatttt tatttttttac ggggataatt ttatataaga caaataatag    2460
agttgctagt gttgaagaaa gcttaaataa tatatctagt tcagtaactg gattagttaa    2520
agggactta aagttttggt acagtgaaga agacaaaaaa gcctatgtaa gtaatgtaga    2580
aagtattaaa aaaaataaag atagcaagaa gaaaaaataa aagcttcagt aagataaaaa    2640
agcaataaac atttaattta ttgctttttt atttttatagt ttagtcattg agggtaaatt    2700
tttatagtaa tatatattac aacaatatta ctatattact ttttaacatt ctttagaaac    2760
atatccataa tatagttcat tagacttgcg acagttattc catttgtagc agcatacttt    2820
ttgaaatttg agtaaatctc tgagtttgtt ttcattgata tagttatatc attttttaaa    2880
gttctataat gttcaggaag tacaacagtt tcattattta cattaattt tctttcgtta    2940
acaatattaa aaagtatttc taaattttct tcattaaaca aactattata tttttctgga    3000
actgtcaatt gaaattcttg cttttcattt atattacttt ttatattact atctatatta    3060
cttacacttt cagtaacttc ttcttcaggc ttcacaaaat cttttaaagt ttcatcaaca    3120
taagtcataa cagcttttttt tatccctttt ggagcataat taacttttac atcatctatg    3180
aatgtaacat cataagttcc attctctagt tttgtaatct cattaatttt ttctaaatat    3240
tttttagcaa gacccaaacc ttgtaccata aaaaatcact cccctttta tcttagtaat    3300
atatattact ataatattac taaattttaa catagcataa atacacaagt tcaatcggta    3360
atatttatta ctacaatatt actttattac ttcaacagta tacacctgtt tttataaaaa    3420
ataaagagtt ttttttatgc agaaaaaata ttaaaataaa ttttataaaa aatctctaaa    3480
```

-continued

```
atcatttta aggctttta ttttattgag ccatacttt tattgttaaa atgtctaaaa     3540
tcatttttag gggtatccta ggactttaa attgatttta aatgctgttt gtgtgttaaa    3600
cttctttatg ttttttaaa taaaaagt taggcattgt gagagtccta acttttatg      3660 tcgttttgtt caagcaacgg atactttgtt gctatgtttc aaactaatta tatcacattc   3720 aattttaat ttcaatatgt tattaattct aattgtcgtt tcctccaaag gaggtgaaag    3780
atgttcaagg aatggatact attgataatg ctttaatat ttattgctat tttacaatat    3840
gcagttatat taatatggtt tcacattatc acaagtttat tagcatagtt cttgtaaaaa   3900
ataatgctag agagttagta aagtgtgaga gcttgaaaac tctctttttt tttagggaaa   3960
catatttata tttattttca atcttttta ccgaaagttg attttccact ttcggtaatt    4020
ttttatattt ttttattgag cttctttat taaaaaaat cacattacta atatgattaa     4080
tataataata ttataata atatataata cagcactcat ttttctttt aatagcaatg     4140 taaacaaaa agataacagg acaaattttc aactttaaca ggacaaattt tcaacttta    4200 caggacaaat tttcaacttt aacaggacaa attttcaact ttaacaggac aaattttcaa   4260
ctttaacagg acaaattttc aactttaaca ggacaaattt cattgacagt cttatattat   4320
tggtgtataa tgttttatg aaataaaatt tccataaaag gagctgaaga ttttagtgaa    4380
taatgattta gtaaaagtac ataaagattt taccaaatta aatataggga cattaagtga   4440 aaagaatta gaattatttt attatatatg tttaaatgta aaggatatta gagatgaaat    4500
tataacaatg gattttctt ctataaaaaa aagtttaggt ttaattaatt ttagagattt    4560
aaaaaaatat attttaggac ttcatcaaaa attaggaaat ttacatatta ctaatataac   4620
aaataaaaaa attgaaacaa tctttttatt tgaaaaattc ataaatgatt tagataataa   4680
tactttaact ataagagtaa caaaagattc tctttatttt tttaatattg ctaacagtta   4740
tttaaggttt ctcttttcag atgttagaaa actttcagga aaatattcaa agttattggt   4800
tccttattta atggagttta gtcataaaaa agaagctgaa tttgaaaaag agagattttt   4860
taatattcta gaagttgaag aaagttatag aaataattta tcagatttta ataagagaat   4920
tctaaaacca gctgttgaag aattaaaaac acttttgaa aatttaaagg ttgagcgatt    4980
aaaaaatgga agagtaataa aaggatataa atttagctgg actaatgatt ttaattttca    5040
aaataagaaa gataatatag aagaagcaga agtagtggaa gaaaagaaa atattgcttc     5100 aggagagtta gaaaaatatt ttaaatcaac tttactgat gtaaattatt caagaagca     5160 taaagaagtt ttagaaaaat tattaaaaaa taatagttta gaatatatta aaaaatattt   5220
atctgagcag tgggagtatg tacaaaatga taaaaatatt ttaaataaat cagcatattt   5280
ctcaaaacta atttagaag aaaaagcagt atataaaaat catctaccag ctgactatga    5340 agaactaaa gttgaagaaa gaaatagaaa tatagaaagt acaaatacta ttacatcatt    5400
aaaagattta gtagaaaaag acattacaga ttatgaagtt agaagaata taactcctga    5460 acaaatagaa caagagtttt tatttaaaat agatgtaact gaagaagaat ataataagat   5520
taaagaagat tggataataa aacgaaaaga tgaagttcct aatagtgatc caaaactttt   5580
agaaattata tttaatgcaa gtcaatcaaa aaaatataat ataattaata ctaaagaaga   5640
agttaatgaa aaagaaaaag agcttcacga attagaagaa aatataaaaa gaatgcaaga   5700
agaactaaat aaattaaaaa aagaggtata gtataatacc tctttctttt tttaagtggc   5760
ttaaaattga ttttagagct tcattttttt tcaacttttt ctttttcttc ctttctata    5820
```

```
tctttttttta gttgacgaat aaaattaatt acttttttcta aattaaaatc atctaaatct    5880
ttaaatt                                                                5887
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:rlx
      oligonucleotide PCR custom primer

<400> SEQUENCE: 7

```
cctggtgaag tagatgaag                                                   19
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:repA
      oligonucleotide PCR custom primer

<400> SEQUENCE: 8

```
ttagttttag caatggaag                                                   19
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:repA
      oligonucleotide PCR custom primer

<400> SEQUENCE: 9

```
atgctggagt gtgatatg                                                    18
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:repA
      oligonucleotide PCR custom primer

<400> SEQUENCE: 10

```
gttgattttc cactttcgg                                                   19
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:imperfect
      repeat of iteron

<400> SEQUENCE: 11

```
taaactttaa caggacaaat tt                                               22
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:imperfect
      repeat of iteron

<400> SEQUENCE: 12

-continued

```
tcaactttaa caggaccaat tt                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:imperfect
      repeat of iteron

<400> SEQUENCE: 13
tcaactttat caggacaaat tt                                              22

<210> SEQ ID NO 14
<211> LENGTH: 951
<212> TYPE: DNA
<213> ORGANISM: Artificial Sequence
<220> FEATURE:
<223> OTHER INFORMATION: Description of Artificial Sequence:partial
      sequence of plasmid pFN3
<221> NAME/KEY: modified_base
<222> LOCATION: (1)..(951)
<223> OTHER INFORMATION: n = g, a, c or t

<400> SEQUENCE: 14
atgattattg gtataataaa ctataaaata tagatttcat ttttaaaggc tttatatagt      60
gttttttaaa gttttagtat ttaagttata atttatacct gtataccttt aaaaacttta    120
aatttatata tgctatcaat tttaaatggt atttatttta ttattatgtt tctattttta    180
aaaataacaa taaatataaa atataaatag aataataaag ttatggttat taatatttta    240
aaaaaaatat aaagtaaaat tttgtaaaaa tttactctta tattttaaca taaaaaaatt    300
gtgaagacaa tttatttatg tggtttaaaa atatataatc ttcatttttt tgaagacttc    360
acttatcact tatttaatgt tagaataaca ataaataatg aaagtgaggc gataaaaaaa    420
tggaaaatat taagaagaaa aaaantantt tanntgcant aattaaagtc ctagaaacat    480
ataatataaa tgcaantgac ttaaaaaaat tanatgaatt acaaataata naacanaaaa    540
atttagatat tataaaacta ttaactaagt tagaaagtgg ttntaaaagt naaaaaatan    600
aatttgctac agctgangaa acacangaaa aaattttaaa caattttaaa tgatatagtt    660
ccagcaacta aaanaaatna cnaaaaacnt ncagaacaac accantttag aaaatnatnt    720
nnatagttca aanaaatnac ttcgngagag gtctgnttaa gacacttcaa nnttaanaga    780
ggnattatta tatacccccct tgtttttaaa tttattttt aaatatactt gctatntcgc    840
cgnaattggg ctgcttcnat nctgctgctt tttnccnaga aattcctatn attttttcctc   900 ttaacccact tttaaattaa nntcntncct tttccnttnt ttccctnttg n             951

<210> SEQ ID NO 15
<211> LENGTH: 9955
<212> TYPE: DNA
<213> ORGANISM: Artificial Sequence
<220> FEATURE:
<223> OTHER INFORMATION: Description of Artificial Sequence:plasmid
      pHS17

<400> SEQUENCE: 15
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc   120
tcgccacgtt cgccggcttt ccccgtcaag ctctaaatcg ggggctccct ttagggttcc   180
```

-continued

```
gatttagtgc tttacggcac ctcgacccca aaaaacttga ttagggtgat ggttcacgta    240
gtgggccatc gccctgatag acggttttc gcccttgac gttggagtcc acgttcttta     300
atagtggact cttgttccaa actgaacaa cactcaaccc tatctcggtc tattcttttg    360
atttataagg gattttgccg atttcggcct attggttaaa aaatgagctg atttaacaaa   420
aatttaacgc gaattttaac aaaatattaa cgcttacaat ttccattcgc cattcaggct   480
gcgcaactgt tgggaagggc gatcggtgcg ggcctcttcg ctattacgcc agctggcgaa   540
agggggatgt gctgcaaggc gattaagttg gtaacgcca gggttttccc agtcacgacg    600
ttgtaaaacg acgccagtg aattgtaata cgactcacta tagggcgaat tgggtacccc    660
cgatagcttc cgctattgct ttttgctca tcggtatttg caacatcata gaaattgcat    720 accttttgttc ctcggttata tgtttgctca tctgcaactt ttttttcttt ggacggacaa   780
ttaaagcaaa gatagcaaac tttatccatt cagagtgaga gaaggggga cattgtctct    840 ctttcctctc tgaaaaataa atgttttat tgcttattat ccgcacccaa aaagttgcat    900
ttataagttg aactcaagaa gtattcacct gtaagaagtt actaatgaca aaaagaaat     960 tgcccgttcg ttttacgggt cagcacttta ctattgataa agtgctaata aaagatgcaa  1020
taagacaagc aaatataagt aatcaggata cggttttaga tattggggca ggcaaggggt  1080
ttcttactgt tcattatta aaatcgcca acaatgttgt tgctattgaa acgacacag      1140 ctttggttga acatttacga aaattatttt ctgatgcccg aaatgttcaa gttgtcggtt  1200 gtgatttag gaattttgca gttccgaaat tccctttcaa agtggtgtca atattcctt     1260 atggcattac ttccgatatt ttcaaaatcc tgatgtttga gagtcttgga aattttctgg  1320
gaggttccat tgtccttcaa ttagaaccta cacaaaagtt attttcgagg aagctttaca  1380
atccatatac cgttttctat catacttttt ttgatttgaa acttgtctat gaggtaggtc  1440
ctgaaagttt cttgccaccg ccaactgtca aatcagccct gttaaacatt aaagaaaac   1500 acttattttt tgattttaag tttaaagcca aatacttagc atttatttcc tgtctgttag   1560
agaaacctga tttatctgta aaaacagctt taaagtcgat tttcaggaaa agtcaggtca  1620
ggtcaatttc ggaaaaattc ggtttaaacc ttaatgctca aattgtttgt ttgtctccaa   1680
gtcaatggtt aaactgtttt ttggaaatgc tggaagttgt ccctgaaaaa tttcatcctt   1740
cgtagttcaa agtcgggtgg ttgtcaagat gattttttg gtttggtgtc gtctttttt    1800 aagctgccgc ataacggctg gcaaattggc gatggagcgg aaacgtaaaa gaagttatgg   1860
aaataagact tagaagcaaa cttaagagtg tgttgatagt gcagtatctt aaaattttgt   1920
ataataggaa ttgaagttaa attagatgct aaaaatttgt aattaagaag gagtgattac   1980
atgaacaaaa atataaaata ttctcaaaac tttttaacga gtgaaaaagt actcaaccaa   2040
ataataaaac aattgaattt aaaagaaacc gataccgttt acgaaattgg aacaggtaaa   2100 gggcattaa cgacgaaact ggctaaaata agtaaacagg taacgtctat tgaattagac    2160
agtcatctat tcaacttatc gtcagaaaaa ttaaaactga atactcgtgt cactttaatt   2220
caccaagata ttctacagtt tcaattccct aacaaacaga ggtataaaat tgttgggagt   2280
attccttacc atttaagcac acaaattatt aaaaaagtgg ttttttgaaag ccatgcgtct  2340 gacatctatc tgattgttga agaaggattc tacaagcgta ccttggatat tcaccgaaca   2400
ctagggttgc tcttgcacac tcaagtctcg attcagcaat tgcttaagct gccagcggaa   2460
tgctttcatc ctaaaccaaa agtaaacagt gtcttaataa aacttacccg ccataccaca   2520
gatgttccag ataaatattg gaagctatat acgtactttg tttcaaaatg ggtcaatcga   2580
```

```
gaatatcgtc aactgtttac taaaaatcag tttcatcaag caatgaaaca cgccaaagta    2640
aacaatttaa gtaccgttac ttatgagcaa gtattgtcta ttttaatag ttatctatta     2700 tttaacggga ggaaataatt ctatgagtcg cttttgtaaa tttggaaagt tacacgttac    2760
taaagggaat gtagataaat tattaggtat actactgaca gcttcgggga tcctctagag    2820
tcgacctgca gcccggggga tccactagtt ctaggacttt taaattgatt ttaaatgctg    2880
tttgtgtgtt aaacttcttt atgttttttt aaataaaaaa agttaggcat tgtgagagtc    2940 ctaactttt atgtcgtttt gttcaagcaa cggatacttt gttgctatgt ttcaaactaa     3000
ttatatcaca ttcaatttt aatttcaata tgttattaat tctaattgtc gtttcctcca    3060
aaggaggtga aagatgttca aggaatggat actattgata atggctttaa tatttattgc    3120 tatttacaa tatgcagtta tattaatatg gtttcacatt atcacaagtt tattagcata    3180
gttcttgtaa aaaataatgc tagagagtta gtaaagtgtg agagcttgaa aactctcttt    3240 tttttaggg aaacatattt atatttattt tcaatctttt ttaccgaaag ttgattttcc    3300
actttcggta attttttata tttttttatt gagcttcttt tattaaaaaa atcacatta    3360 ctaatatgat taatataata atattatata ataatatata atacagcact cattttctt    3420 tttaatagca atgtaaaaca aaaagataac aggacaaatt ttcaacttta acaggacaaa    3480
ttttcaactt taacaggaca aattttcaac tttaacagga caaattttca actttaacag    3540
gacaaatttt caactttaac aggacaaatt ttcaacttta acaggacaaa tttcattgac    3600
agtcttatat tattggtgta taatgttttt atgaaataaa atttccataa aaggagctga    3660
agattttagt gaataatgat ttagtaaaag tacataaaga ttttaccaaa ttaaatatag    3720
ggacattaag tgaaaaagaa ttagaattat tttattat atgtttaaat gtaaaggata    3780
ttagagatga aattataaca atggattttt cttctataaa aaaaagttta ggttaatta    3840 attttagaga tttaaaaaaa tatattttag gacttcatca aaaattagga aatttacata    3900
ttactaatat aacaaataaa aaaattgaaa caatctttt atttgaaaaa ttcataaatg    3960
atttagataa taatacttta actataagag taacaaaaga ttctctttat tttttaata    4020 ttgctaacag ttatttaagg tttctctttt cagatgttag aaaactttca ggaaaatatt    4080
caaagttatt ggttccttat ttaatggagt ttagtcataa aaaagaagct gaatttgaaa    4140
aagagagatt ttttaatatt ctagaagttg aagaaagtta tagaaataat ttatcagatt    4200
ttaataagag aattctaaaa ccagctgttg aagaattaaa aacactttt gaaaatttaa    4260 aggttgagcg attaaaaaat ggaagagtaa taaaggata taaatttagc tggactaatg    4320
attttaattt tcaaaataag aaagataata tagaagaagc agaagtagtg gaagaaaaag    4380
aaaatattgc ttcaggagag ttagaaaaat attttaaatc aactttact gatgtaaatt    4440 attcaaagaa gcataaagaa gttttagaaa aattattaaa aaataatagt ttagaatata    4500
ttaaaaaata tttatctgag cagtgggagt atgtacaaaa tgataaaaat atttaaata    4560 aatcagcata tttctcaaaa ctaatttag aagaaaagc agtatataaa aatcatctac    4620
cagctgacta tgaagaacta aaagttgaag aaagaaatag aaatatagaa agtacaaata    4680
ctattacatc attaaaagat ttagtagaaa aagacattac agattatgaa gttagaaaga    4740
atataactcc tgaacaaata gaacaagaag ttttatttaa aatagatgta actgaagaag    4800
aatataataa gattaaagaa gattggataa taaaacgaaa agatgaagtt cctaatagtg    4860
atccaaaact tttagaaatt atatttaatg caagtcaatc aaaaaaatat aatataatta    4920
```

```
atactaaaga agaagttaat gaaaaagaaa aagagcttca cgaattagaa gaaaatataa    4980
aaagaatgca agaagaacta aataaattaa aaaaagaggt atagtataat acctctttct    5040 tttttttaagt ggcttaaaat tgattttaga gcttcatttt ttttcaactt tttctttttc    5100
ttccttttct atatctttttt ttagttgacg aataaaatta attactttttt ctaaattaaa    5160 atcatctaaa tctttaaatt catataataa ctttttgttt ctttcttcta gtactttttt    5220
ttctaactct tttaatttct ttttactttt tcaattttt tctaattcaa tcgcttttaa     5280
ttcttctaaa gtcttttaa tttttttagt agcttccata catatcacac tccagcatta     5340
ttatttataa aaatataatt atatataaca tatctagtaa aataaatcaa gtagtgtcgg    5400
cttaaacaag agccatataa attaaaaaat atatatattt ttcttttaat ttctaatata    5460
aaatggtata atattttata tggcattgtt taaggcaagc tactcactcc tgccgtcgtg    5520
tagcttgctg ggaagtatcc cagaccctca gaagcaccta caaaaattaa aaatatattt    5580
ttaattttct tcggtactta taggggatg accccctata cccctgcgag ttgattttat     5640
aaaattcttg cagggacagc tgcaattatt ttataaaacc aactttaaag agagtgataa    5700
taatgattaa atttcacatta agattaataa taatgattaa atttacatta agattaacgg    5760
aagatgaaaa aaacttttta gatataaaag ctgatgaatt aggtaaatca aaaaatgaag    5820
ttttaaagtt tcttataaac aataaattgg aagatactaa aaaagaattt gacctattaa    5880
atgagcttga taaaaattat aaagagctag gttttcagat taaaaaaatt ggagtagttt    5940
taaatcagat taataaaaat ttttatgaag ataagaaaat acagattgaa gaaatccaag    6000
gagcgttaga tgaattatgg cagtctataa aagtgtcaaa ggagtaggaa aaactaaaag    6060
cagtttatac aatattttaa agtatgtagg aagtcaaaat gaaaagaaa aagatgatag    6120 agtttataaa actactggta taaatgttag tgatgattat aaaaaagctt ttaaagaaat    6180
gatgttaaca aaagagcttc attgtaagtt agacggtaga caatatagac accatattca    6240
atctttaaaa cctggtgaag tagatgaaga aacagcacat aaaatggcag tagaatttgc    6300
agaaaaaaat tttaaaggct tgatgttttt tatatcaact cacattgata aaggacacat    6360
acataaccat ataattatta atactgttaa tattgatact ggaatgaagt tcagagaatt    6420
aaataagaat gaatataatc aaaaaaaaga aaataatgtt gaattaaaat ctcacgaatt    6480
ttatttagaa gatttaaaaa aatctagtga tgaaatttgt cttgcaaata atttatcggt    6540
gatcccccaa aaagaaaaag ctgaaagtca gaatatttat aatagacgag aatataatgt    6600
tgtgatgaac aaaacaagtt ataaaatgga gctggcaaaa gatataaaaa gagcttccaa    6660
gaattgtaaa tcaaagaag attttataaa agcattagat gaaaaggtg ttattgtgga    6720 ttgggaagac cataaaaaac atataacttt taaatttaaa gatgagaaaa agaaatcaat    6780
tagattagca aatttagaaa aaactttcca agatgaaact tttaaaaagg aatacctgga    6840
acagcaattt ttaataaatc aaaaaactga agaaatagga aatttcaaaa ttaaagttaa    6900
tactgaagct gaaaaaacta atgaagaaaa atatcaagag cttctaaata aaagagaga    6960 acaagataaa ttaatagctg aagaaaaatt gaaaagcaa aaagaagaaa ttgagaaaaa    7020
gaaaatttta aatagaaaca aaggtttcgg aataggagat taaaaatggc tatattagat    7080
gatgatgtaa atgaagttaa aaatgtgaat gagcaagaaa taaaaatgga tagttatatt    7140
aaaaaaataa ttgaaaatgt tttagaagtt cagctaaaag aacataaaga aatagcttcc    7200
attgctaaaa ctaaaatagc tgaagtaact ttagaactag aaaaattaaa acagctggag    7260
aaagcaacta ctaaatatag agatgataca aatataatta caaataaaat gattgaaaat    7320
```

-continued

```
gttgaaaatt ataataaagt atttttagaa agaattgata aatttaattt attgatggta      7380
gaaaagttaa atgaagtaaa aaatactaat caaatatttg ctgagacatt agataaatca      7440
gatattgttg ataaccttaa taagagtaga gcagaaatat ttgagaaatt ttcaactgat      7500
gttgctacaa aaacaaataa tacttttaat ttaattgaag atagtctaaa taaattaaaa      7560
atagccttct atacagctgt atctgttatt gtaatatttt tatttttttac ggggataatt      7620 ttatataaga caaataatag agttgctagt gttgaagaaa gcttaaataa tatatctagt      7680
tcagtaactg gattagttaa aggggactta aagttttggt acagtgaaga agacaaaaaa      7740
gcctatgtaa gtaatgtaga aagtattaaa aaaaataaag atagcaagaa gaaaaaataa      7800
aagcttcagt aagataaaaa agcaataaac atttaattta ttgcttttttt attttatagt      7860 ttagtcattg agggtaaatt tttatagtaa tatatattac aacaatatta ctatattact      7920
ttttaacatt ctttagaaac atatccataa tatagttcat tagacttgcg acagttattc      7980
catttgtagc agcatacttt ttgaaatttg agtaaatctc tgagtttgtt ttcattgata      8040
tagttatatc attttttaaa gttctataat gttcaggaag tacaacagtt tcattattta      8100
cattaatttt tctttcgtta acaatattaa aaagtatttc taaattttct tcattaaaca      8160
aactattata ttttttctgga actgtcaatt gaaattcttg cttttcattt atattacttt      8220
ttatattact atctatatta cttacacttt cagtaacttc ttcttcaggc ttcacaaaat      8280
cttttaaagt ttcatcaaca taagtcataa cagctttttt tatcccttttt ggagcataat      8340 taactttttac atcatctatg aatgtaacat cataagttcc attctctagt tttgtaatct      8400 cattaattttt ttctaaatat tttttagcaa gacccaaacc ttgtaccata aaaaatcact      8460 cccctttttta tcttagtaat atatattact ataaatattac taaatttttaa catagcataa      8520 atacacaagt tcaatcggta atatttatta ctacaatatt actttattac ttcaacagta      8580
tacacctgtt tttataaaaa ataaagagtt ttttttatgc agaaaaaata ttaaaataaa      8640
ttttataaaa aatctctaaa atcatttttta aggctttttta ttttattgag ccatacttttt      8700 tattgttaaa atgtctaaaa tcattttttag gggtatccta gagcggccgc caccgcggtg      8760
gagctccagc ttttgttccc tttagtgagg gttaatttcg agcttggcgt aatcatggtc      8820
atagctgttt cctgtgtgaa attgttatcc gctcacaatt ccacacaaca tacgagccgg      8880
aagcataaag tgtaaagcct ggggtgccta atgagtgagc taactcacat taattgcgtt      8940
gcgctcactg cccgctttcc agtcgggaaa cctgtcgtgc cagctgcatt aatgaatcgg      9000
ccaacgcgcg gggagaggcg gtttggtatt gggcgctctt ccgcttcctc gctcactgac      9060
tcgctgcgct cggtcgttcg gctgcggcga gcggtatcag ctcactcaaa ggcggtaata      9120
cggttatcca cagaatcagg ggataacgca ggaaagaaca tgtgagcaaa aggccagcaa      9180
aaggccagga accgtaaaaa ggccgcgttg ctggcgtttt tccataggct ccgcccccct      9240
gacgagcatc acaaaaatcg acgctcaagt cagaggtggc gaaacccgac aggactataa      9300
agataccagg cgtttccccc tggaagctcc ctcgtgcgct ctcctgttcc gaccctgccg      9360
cttaccggat acctgtccgc ctttctccct tcgggaagcg tggcgctttc tcatagctca      9420
cgctgtaggt atctcagttc ggtgtaggtc gttcgctcca agctgggctg tgtgcacgaa      9480
ccccccgttc agcccgaccg ctgcgcctta tccggtaact atcgtcttga gtccaacccg      9540
gtaagacacg acttatcgcc actggcagca gccactggta acaggattag cagagcgagg      9600
tatgtaggcg gtgctacaga gttcttgaag tggtggccta actacggcta cactagaagg      9660
```

-continued

```
acagtatttg gtatctgcgc tctgctgaag ccagttacct tcggaaaaag agttggtagc    9720
tcttgatccg gcaaacaaac caccgctggt agcggtggtt tttttgtttg caagcagcag    9780
attacgcgca gaaaaaaagg atctcaagaa gatcctttga tcttttctac ggggtctgac    9840
gctcagtgga acgaaaactc acgttaaggg attttggtca tgagcggata catatttgaa    9900
tgtatttaga aaaataaaca aatagggggtt ccgcgcacat ttccccgaaa agtgc        9955
```

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:forward
      primer to amplify repA

<400> SEQUENCE: 16
gacattaagt gaaaaag                                                   17

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:reverse
      primer to amplify repA

<400> SEQUENCE: 17
atgctggagt gtgatatg                                                  18

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:forward
      primer to amplify the origin of replication including the AT-rich
      region, the iteron repeat sequences and the putative DnaA binding
      sites

<400> SEQUENCE: 18
acggatactt tgttgct                                                   17

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:reverse
      primer to amplify the origin of replication including the AT-rich
      region, the iteron repeat sequences and the putative DnaA binding
      sites

<400> SEQUENCE: 19
tatcctttac attta                                                     15

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence:forward
      primer to amplify the combined origin of replication and repA
      sequences

<400> SEQUENCE: 20
acggatactt tgttgct                                                   17

```
<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:reverse
      primer to amplify the combined origin of replication and repA
      sequences

<400> SEQUENCE: 21
atgctggagt gtgatatg                                                    18
```

What is claimed is:

1. An isolated origin of replication functional in *Fusobacterium nucleatum* that comprises at least two copies of an iteron, the iteron comprising a nucleic acid sequence of SEQ ID NO:3.

2. The isolated origin of replication of claim 1, wherein the isolated origin of replication comprises two to six copies of the iteron.

3. The isolated nucleic acid of claim 1, wherein the isolated origin of replication comprises a nucleic acid sequence of SEQ ID NO:4.

4. The isolated nucleic acid of claim 1, wherein the isolated origin of replication comprises a nucleic acid sequence of nucleotide position 3936 to 4481 of SEQ ID NO:6.

5. A nucleic acid encoding a RepA protein functional in *F. nucleatum*, wherein the nucleic acid:

(a) is separated from open reading frames that flank the nucleic acid as found in its native state, and (b) the nucleic acid encodes a protein that comprises greater than about 90% amino acid sequence identity to SEQ ID NO:1.

6. The nucleic acid of claim 5, wherein the nucleic acid encodes a polypeptide comprising SEQ ID NO:1.

7. The nucleic acid of claim 5, wherein the nucleic acid encodes a polypeptide having a molecular weight of about 44.8 kDa.

8. The nucleic acid of claim 5, wherein the nucleic acid is from *F. nucleatum*.

9. The nucleic acid of claim 5, wherein the nucleic acid comprises SEQ ID NO:2.

10. An isolated plasmid for replicating in *F. nucleatum*, the plasmid comprising a nucleic acid encoding a RepA protein functional in *F. nucleatum*, the nucleic acid:

(a) encoding a protein comprising greater than about 90% amino acid sequence identity to SEQ ID NO:1 provided that the nucleic acid encoding the RepA protein is not SEQ ID NO:5.

11. The plasmid of claim 10, wherein the nucleic acid encodes a polypeptide comprising SEQ ID NO:1.

12. The plasmid of claim 10, wherein the nucleic acid comprises SEQ ID NO:2.

13. A method of transforming *F. nucleatum* with the plasmid of claim 10, the method comprising:

contacting the plasmid with *F. nucleatum* in liquid media under conditions that allow the plasmid to be internalized by *F. nucleatum* and thereby, creating transformants.

14. The plasmid of claim 10, the plasmid further comprising a marker gene.

15. The plasmid of claim 14, wherein the marker gene is an antibiotic resistance gene.

16. A host cell comprising the plasmid of claim 14.

17. The host cell of claim 16, wherein the host cell is *F. nucleatum*.

18. An isolated RepA protein functional in *F. nucleatum*, the RepA protein comprising;

(a) greater than about 90% amino acid sequence identity to SEQ ID NO:1.

19. The isolated RepA protein of claim 18, wherein the the polypeptide comprises greater than about 97% sequence identity to SEQ ID NO:1.

20. The isolated RepA protein of claim 18, wherein the polypeptide is SEQ ID NO:1.

21. An isolated plasmid for replicating in *F. nucleatum*, the plasmid comprising an origin of replication that comprises at least two copies of an iteron, the iteron comprising the nucleic acid sequence of SEQ ID NO:3.

22. The plasmid of claim 21, wherein the origin of replication comprises between two to six copies of the iteron.

23. The plasmid of claim 21, wherein the origin of replication comprises a nucleic acid sequence of SEQ ID NO:4.

24. A method of transforming *F. nucleatum* with the plasmid of claim 21, the method comprising:

contacting the plasmid with *F. nucleatum* in liquid media under conditions that allow the plasmid to be internalized by *F. nucleatum* and thereby, creating transformants.

25. The plasmid of claim 21, wherein the origin of replication is recombinantly inserted into the plasmid.

26. The plasmid of claim 25, wherein a nucleic acid encoding an *F. nucleatum* RepA protein is recombinantly inserted into the plasmid.

27. The plasmid of claim 21, the plasmid further comprising a marker gene.

28. The plasmid of claim 27, wherein the marker gene is an antibiotic resistance gene.

29. A host cell comprising the plasmid of claim 27.

30. The host cell of claim 29, wherein the host cell is *F. nucleatum*.

31. The plasmid of claim 21, the plasmid further comprising a nucleic acid encoding a RepA protein functional in *F. nucleatum*, the nucleic acid:

(a) encoding a protein that comprises greater than about 90% amino acid sequence identity to SEQ ID NO:1 provided that the nucleic acid encoding the RepA protein is not SEQ ID NO:5.

32. The plasmid of claim 31, wherein the nucleic acid encodes a polypeptide comprising SEQ ID NO:1.

33. The plasmid of claim 31, wherein the nucleic acid comprises SEQ ID NO:2.

34. The plasmid of claim 31, the plasmid further comprising a transcription cassette comprising a nucleic acid of interest operably linked to a promoter.

35. A method of transforming *F. nucleatum* with the plasmid of claim 31, the method comprising:

contacting the plasmid with *F. nucleatum* in liquid media under conditions that allow the plasmid to be internalized by *F. nucleatum* and thereby, creating transformants.

36. The plasmid of claim 31, the plasmid further comprising at least one marker gene.

37. The plasmid of claim 36, wherein the marker gene is an antibiotic resistance gene.

38. A host cell comprising the plasmid of claim 36.

39. The host cell of claim 38, wherein the host cell is *F. nucleatum*.

40. A shuttle vector comprising an origin of replication functional in *Esherichia coli* and an origin of replication functional in *F. nucleatum*, wherein the origin of replication functional in *F. nucleatum* comprises at least two copies of an iteron comprised of SEQ ID NO:3.

41. The shuttle vector of claim 40, wherein the origin of replication functional in *F. nucleatum* comprises between two to six copies of the iteron.

42. The shuttle vector of claim 40, wherein the origin of replication functional in *F. nucleatum* comprises a nucleic acid sequence of SEQ ID NO:4.

43. The shuttle vector of claim 40, wherein the origin of replication functional in *F. nucleatum* comprises a nucleic acid sequence of nucleotide position 3936 to 4481 of SEQ ID NO:6.

44. A method of transforming *F. nucleatum* with the shuttle vector of claim 40, the method comprising:

contacting the plasmid with *F. nucleatum* in liquid media under conditions that allow the plasmid to be internalized by *F. nucleatum* and thereby, creating transformants.

45. A method of transforming *E. coli* with the shuttle vector of claim 40, the method comprising:

contacting the plasmid with *E. coli* in liquid media under conditions that allow the plasmid to be internalized by *E. coli* and thereby, creating transformants.

46. A host cell comprising the shuttle vector of claim 40.

47. The host cell of claim 46, wherein the host cell is *F. nucleatum*.

48. The host cell of claim 46, wherein the host cell is *Escherichia coli*.

49. The shuttle vector of claim 40, the vector further comprising a nucleic acid encoding a RepA protein functional in *F. nucleatum*, the nucleic acid:

(a) encoding a protein that comprises greater than about 90% amino acid sequence identity to SEQ ID NO:1.

50. The shuttle vector of claim 49, wherein the nucleic acid encoding the RepA protein functional in *F. nucleatum* encodes a polypeptide comprising SEQ ID NO:1.

51. The shuttle vector of claim 49, wherein the nucleic acid encoding the RepA protein for *F. nucleatum* comprises SEQ ID NO:2.

52. The shuttle vector of claim 49, wherein the vector comprises an ermF-ermAM cassette.

53. The shuttle vector of claim 49, the vector further comprising a transcription cassette comprising a nucleic acid of interest operably linked to a promoter.

54. The shuttle vector of claim 49, the vector further comprising at least one marker gene.

55. The shuttle vector of claim 54, wherein the marker gene is an antibiotic resistance gene.

56. An isolated nucleic acid molecule comprising a 2.36 kb DNA fragment generated by cleavage of SEQ ID NO:6 with restriction endonucleases AvrII and ScaII.

57. An isolated plasmid designated pFN1 that has a nucleotide sequence corresponding to SEQ ID NO:6.

58. An isolated plasmid for replicating in *F. nucleatum*, the plasmid comprising a DNA fragment selected from the group consisting of:

a nucleic acid sequence of nucleotide position 3936 to 4481 of SEQ ID NO:6, a 2.36 kb DNA fragment generated by cleaving SEQ ID NO:6 with restriction endonucleases Avr II and ScaII, and a 0.9 kb DNA fragment generated by cleaving plasmid pFN2, which is isolated from ATCC strain deposit number PTA-5816, with restriction endonucleases HincII and HpaII.

59. A method of transforming *F. nucleatum* with the plasmid of claim 58, the method comprising:

contacting the plasmid with *F. nucleatum* in liquid media under conditions that allow the plasmid to be internalized by *F. nucleatum* and thereby, creating transformants.

60. An isolated nucleic acid molecule comprising a 0.9 kb DNA fragment generated by cleaving plasmid pFN2 with restriction endonucleases HincII and HpaII.

61. An isolated plasmid designated pFN2, which is isolated from ATCC strain deposit number PTA-5816, that has partial restriction maps as shown in FIGS. 1A, 3 and 5.

62. An isolated plasmid designated pFN3, which is isolated from ATCC strain deposit number PTA-5815, that has a partial restriction map as shown in FIG. 1A.

63. A shuttle vector designated pHS 17 (SEQ ID NO:15) that has a partial restriction map as shown in FIG. 1A.

* * * * *